(12) United States Patent
Sakamoto et al.

(10) Patent No.: US 7,704,261 B2
(45) Date of Patent: Apr. 27, 2010

(54) LIGATURE AND SUTURE DEVICE FOR MEDICAL APPLICATION, LIGATURE AND SUTURE SYSTEM FOR MEDICAL APPLICATION, AND LIGATURING AND SUTURING METHOD FOR MEDICAL APPLICATION

(75) Inventors: Yuji Sakamoto, Tokyo (JP); Yoshio Onuki, Tokyo (JP); Koh Kimura, Tokyo (JP); Satoshi Miyamoto, Tokyo (JP); Pankaj Jay Pasricha, 3315 Oak Links Ave., Houston, TX (US) 77059; Takayuki Suzuki, Yokohama (JP); Koichi Kawashima, Tokyo (JP)

(73) Assignees: Olympus Corporation, Tokyo (JP); Pankaj Jay Pasricha, Houston, TX (US)

( * ) Notice: Subject to any disclaimer, the term of this patent is extended or adjusted under 35 U.S.C. 154(b) by 453 days.

(21) Appl. No.: 11/099,303

(22) Filed: Apr. 5, 2005

(65) Prior Publication Data

US 2005/0251153 A1 Nov. 10, 2005

Related U.S. Application Data

(60) Provisional application No. 60/560,187, filed on Apr. 7, 2004.

(51) Int. Cl.
*A61B 17/10* (2006.01)
(52) U.S. Cl. ..................................................... 606/139
(58) Field of Classification Search ................. 606/139, 606/144–146; 623/2.11
See application file for complete search history.

(56) References Cited

U.S. PATENT DOCUMENTS

| | | | | |
|---|---|---|---|---|
| 4,898,155 A | * | 2/1990 | Ovil et al. | 606/144 |
| 5,618,270 A | * | 4/1997 | Orejola | 604/164.02 |
| 6,059,800 A | * | 5/2000 | Hart et al. | 606/144 |
| 7,063,715 B2 | * | 6/2006 | Onuki et al. | 606/220 |
| 2002/0040226 A1 | | 4/2002 | Laufer et al. | |
| 2002/0107530 A1 | * | 8/2002 | Sauer et al. | 606/139 |
| 2003/0236535 A1 | | 12/2003 | Onuki et al. | |

FOREIGN PATENT DOCUMENTS

| | | |
|---|---|---|
| JP | 2003-159254 | 6/2003 |
| JP | 2005-110983 | 4/2005 |

* cited by examiner

*Primary Examiner*—(Jackie) Tan-Uyen T. Ho
*Assistant Examiner*—Gregory Anderson
(74) *Attorney, Agent, or Firm*—Scully, Scott, Murphy & Presser, P.C.

(57) ABSTRACT

A ligature and suture device for medical application that ligatures or sutures biomedical tissue that has been suctioned by a suction device using a suturing member. The ligature and suture device includes an insertion portion having a lumen into which an endoscope can be inserted, and a distal end portion that is connected to the lumen and in which at least one side aperture is provided, at least one hollow needle that is able to support inside itself the suturing member, and that is placed inside the insertion portion such that a tip of the hollow needle is able to move between a first position, which is on a base end side of the side aperture, and a second position, which is on a distal end side of the side aperture, an operating section that performs an operation to move the needle, and at least one pledget that can be penetrated by the needle, and that is placed in a vicinity of the distal end of the side aperture so as to be freely removable from the distal end portion.

20 Claims, 34 Drawing Sheets

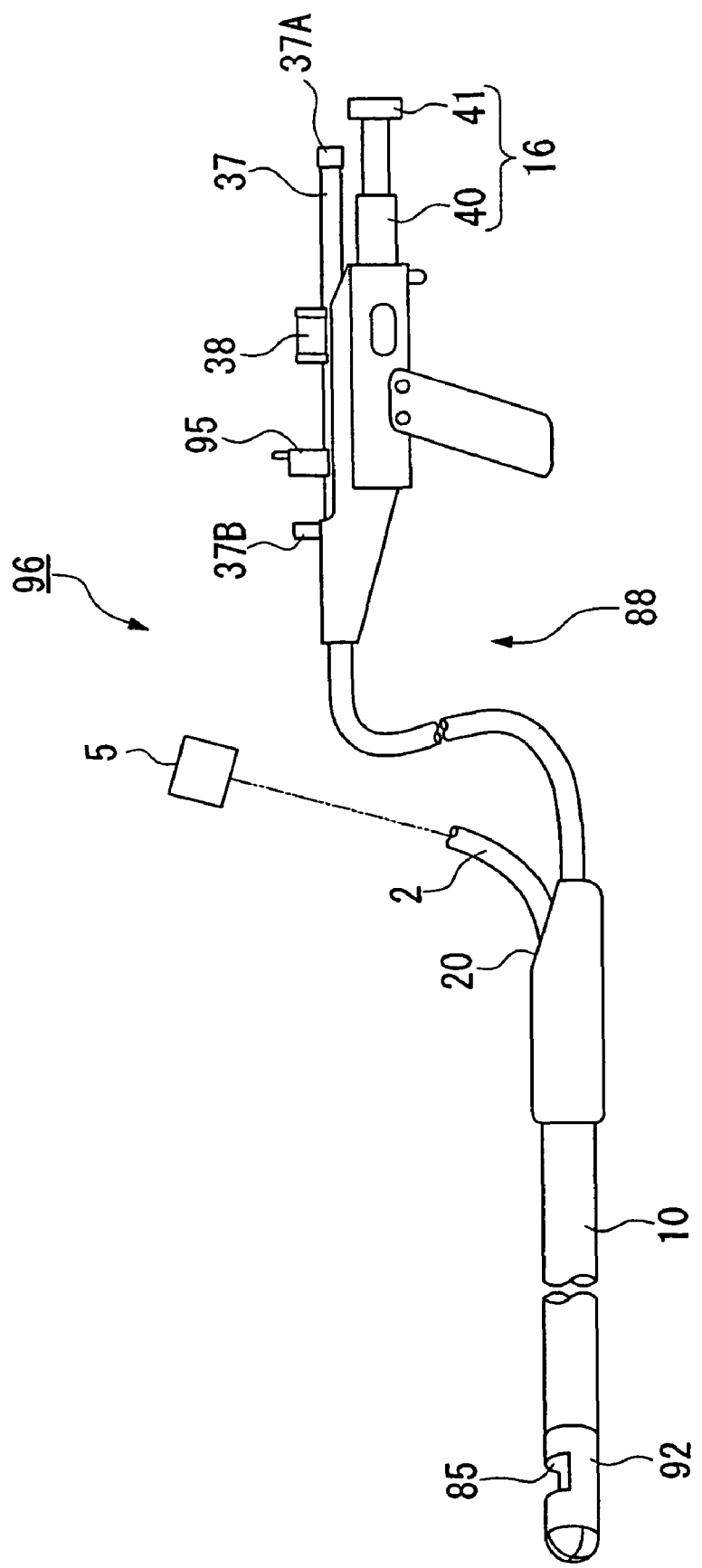

LIGATURE AND SUTURE DEVICE FOR MEDICAL APPLICATION, LIGATURE AND SUTURE SYSTEM FOR MEDICAL APPLICATION, AND LIGATURING AND SUTURING METHOD FOR MEDICAL APPLICATION

The present application claims the benefit of U.S. Provisional Application Ser. No. 60/560,187, filed Apr. 7, 2004, which is incorporated herein by reference.

BACKGROUND OF THE INVENTION

1. Field of the Invention

The present invention relates to a ligature and suture device for medical applications, to a ligature and suture system for medical applications, and to a ligaturing and suturing method for medical applications.

2. Description of Related Art

Conventionally, various instruments have been proposed to suture body tissue using peroral endoscopy. For example, when treating gastroesophageal regurgitation, a ligature and suture device is known that is used to prevent the regurgitation of gastric acid by suturing the biomedical tissue so as to cause it to bulge and thereby forming an artificial valve (see, for example, Patent Documents 1 and 2).

The instrument described in Patent Document 1 is formed such that a suturing member in the form of a hollow needle body, that has a suture thread inserted inside it and that has a T-bar attached to a distal end thereof, performs suturing by being made to penetrate biomedical tissue from one direction, and then being pulled back so that the suture thread is inserted through the biomedical tissue, and the T-bar is anchored in the biomedical tissue.

According to this ligature and suture device for medical applications, because the distal end portion where the ligature treatment is carried out is connected by an elongated, narrow sheath to the operation portion by the hand of an expert operator, instead of sensing by hand the amount of force that is being applied to the tissue when the suture thread is being tightened by the operation section at the operator's hand in order to make the tissue bulge out, the expert operator performs the suturing while verifying the condition of the bulging tissue using an endoscope image.

Moreover, the instrument described in Patent Document 2 is formed such that needles that are penetrated by pledgets are made to approach each other from two directions so as to sandwich biomedical tissue, and the suture thread is inserted through the biomedical tissue.

Furthermore, in order to prevent the suture thread during a ligaturing treatment from biting into the tissue, a suturing member that is provided with a receiving plate member between a T-bar and a stopper that penetrates the suture thread on the operator's side of the T-bar, and also a suturing member that uses a flat T-bar have been proposed (see, for example, Patent Document 3).

(Patent Document 1) Japanese Unexamined Patent Application, First Publication No. 2003-159254

(Patent Document 2) US Patent Application, Publication No. 2002/0040226A1

(Patent Document 3) US Patent Application, Publication No. 2003/0236535A1

SUMMARY OF THE INVENTION

The present invention provides a ligature and suture device for medical application that ligatures or sutures biomedical tissue that has been suctioned by a suction device using a suturing member, the ligature and suture device including: an insertion portion having a lumen into which an endoscope can be inserted, and a distal end portion that is connected to the lumen and in which at least one side aperture is provided; at least one hollow needle that is able to support inside itself the suturing member, and that is placed inside the insertion portion such that a tip of the hollow needle is able to move between a first position, which is on a base end side of the side aperture, and a second position, which is on a distal end side of the side aperture; an operating section that performs an operation to move the needle; and at least one pledget that can be penetrated by the needle, and that is placed in a vicinity of the distal end of the side aperture so as to be freely removable from the distal end portion.

Moreover, the ligature and suture device for medical application according to the present invention is the ligature and suture device for medical application in which the pledget is placed between the distal end of the side aperture and the second position on a movement path of the needle.

The ligature and suture device of the invention for medical application enables biomedical tissue to be taken inside a side aperture in a distal end portion, and, when a needle is made to pierce the biomedical tissue that has been taken in and ligaturing or suturing is conducted using the suturing member, enables a pledget to be placed between the suturing member and the biomedical tissue, and suppresses any burying of the suturing member in the biomedical tissue.

The above ligature and suture device for medical application may further includes a protective member that protects a placement state of the pledget when the endoscope that has been inserted into the lumen is being operated.

According to the ligature and suture device of the invention, it is possible to suppress the pledget from moving or being deformed inside the distal end portion before and after the endoscope is operated, and the pledget can be more suitably pierced by a needle.

In the above ligature and suture device for medical application, the protective member may be placed in the distal end portion.

The ligature and suture device of the invention for medical application enables the pledget placement state to be maintained in a more suitable state in the vicinity of the pledget.

In the above ligature and suture device for medical application, the protective member may be a restricting member that restricts contact between the endoscope that has been inserted into the lumen and the pledget.

In the ligature and suture device of the invention for medical application, because contact between the endoscope and the pledget is restricted by the restricting member, it is possible to restrain the endoscope from coming into contact with the pledget and deforming the pledget, and to maintain the placement state of the pledget.

In the above ligature and suture device for medical application, the protective member may be placed on the pledget.

In the ligature and suture device of the invention for medical application, even if the endoscope and the pledget do come into contact, the placement state of the pledget can be maintained.

The above ligature and suture device for medical application may further include a distal end side needle guide portion that is placed further to the base end side of the distal end portion compared to the pledget, and that guides a distal end of the needle to the pledget.

The ligature and suture device of the invention for medical application enables the needle to be reliably guided to the pledget by causing the needle to be inserted along the distal end side needle guide portion.

In the above ligature and suture device for medical application, a reinforcing portion that increases a rigidity of the distal end portion may be provided in the distal end portion between at least the first position and the second position.

The ligature and suture device of the invention for medical application reduces wavering in the positional relationship between the needle and the side aperture and the pledget using the reinforcing member, and enables wavering of the needle at the moment of piercing by the needle to be suppressed, thereby enabling the needle to be reliably guided to the pledget and pierce the pledget.

In the above ligature and suture device for medical application, a reinforcing portion that increases a rigidity of the distal end portion may be provided in the distal end portion between at least the first position and the distal end side needle guide portion.

In the ligature and suture device of the invention for medical application, when the distal end side needle guide portion is provided, the needle can be reliably guided to the distal end side by the distal end side needle guide portion. Accordingly, the length of the reinforcing portion can be shortened, and the rigid portion of the distal end portion can be reduced to the minimum necessary.

In the above ligature and suture device for medical application, a slit into which the pledget can be press-inserted may be provided so as to open onto a side surface of the distal end portion between the side aperture and the second position.

In the ligature and suture device of the invention for medical application, by press-inserting the pledget in the slit, the pledget can be aligned in a perpendicular direction relative to the movement path of the needle, and penetration by the needle can be reliably performed. Moreover, the pledget can be easily removed by being pulled from the inner side in the radial direction.

In the above ligature and suture device for medical application, the insertion portion may be provided with a pledget anchoring portion that anchors the pledget such that the pledget can be freely removed and anchored again, and the pledget anchoring portion may be formed such that, when the pledget is being moved, at least a portion of the pledget can be removed before the pledget arrives at a distal end of the side aperture, and the pledget anchoring portion is placed a predetermined distance apart from a distal end of the side aperture.

In the ligature and suture device of the invention for medical application, because the pledget anchoring portion is placed a predetermined distance apart from a distal end of the side aperture, the pledget can be deformed by pulling the pledget using the suturing member when the suturing member is moved toward the first position after piercing the pledget, which is anchored at the pledget anchoring portion, by the needle. The pledget can be removed from the slit before the pledget arrives at the distal end of the side aperture, and thus the pledget can be easily removed.

In the above ligature and suture device for medical application, the pledget anchoring portion may be formed as a slit that is placed in the insertion portion, and taking a point that is punctured by the needles when the pledget is anchored in the slit as a needle puncture point, then if the shortest distance from an edge portion of the pledget to the needle puncture point is taken as D, and if the shortest distance from the slit to the needle puncture point is taken as "d", then the predetermined distance L is determined using a Formula:

$$L \geq (D^2 - d^2)^{1/2}.$$

In the ligature and suture device of the invention for medical application, because the pledget does not reach the distal end of the side aperture even when the distance from the slit to the needle puncture point is the minimum value "d" after the pledget is pierced by the needle and is moved toward the side aperture and immediately before being removed from the slit, the pledget can be removed from the slit before it reaches the side aperture.

The above ligature and suture device for medical application may further include jaw portions that are placed on a side surface of the slit, and that protrude gradually towards a terminal end side of the slit.

In the ligature and suture device of the invention for medical application, when the pledget is to be removed from the end of the aperture toward the outside of the distal end, the pledget will not easily come out because the pledget engages the jaw portions. On the other hand, when the pledget is to be removed from the end of the aperture toward the inside of the distal end, the pledget will easily come out while moving along the jaw portions.

The above ligature and suture device for medical application may further include a variable member that alters at least a portion of the width of the slit.

In the ligature and suture device of the invention for medical application, the width of the slit can be changed in accordance with the thickness of the pledget so that the pledget can be pressed in, and the width of the slit can be increased by adjusting the position of the variable member when the pledget is to be removed.

In the above ligature and suture device for medical application, the variable member may be provided with an elastic member that is placed on the side surface on the side aperture side of the slit and that is able to make contact with the pledget.

In the ligature and suture device of the invention for medical application, when the suturing member is moved toward the first position after piercing the pledget by the needle, the width of the slit can be increased by compressively deforming the variable member using the pledget, and thus the pledget can be easily removed.

The above ligature and suture device for medical application may further include: a pledget supporting portion that supports the pledget, and that is provided integrally with the distal end portion, and that is able to change the pledget from being aligned parallel to the needle to being aligned in a direction in which it can be pierced by the needle; and a deforming device that supplies deforming force to the pledget supporting portion.

In the ligature and suture device of the invention for medical application, it is possible to suppress interference between the endoscope and the pledget when the endoscope is inserted into the distal end portion, and only when the needle is inserted in the pledget is the deforming device operated and the pledget support portion deformed, so that the orientation of the pledget can be changed and the needle can be inserted in the pledget.

In the above ligature and suture device for medical application, the pledget supporting portion may be provided integrally with the distal end portion, and the deforming device is the suction device that is able to place the interior of the distal end portion under negative pressure.

In the ligature and suture device of the invention for medical application, only when the biomedical tissue is suctioned by the suction device is the pledget supporting portion deformed, so that the orientation of the pledget can be changed.

In the above ligature and suture device for medical application, the pledget supporting portion may be provided integrally with the distal end portion, and the deforming device may be a wire member having flexibility.

In the ligature and suture device of the invention for medical application, by operating the wire member at the moment of penetration by the needle, the pledget supporting portion can be deformed.

The present invention further provides a ligature and suture system for medical application including: the ligature and suture device for medical application according to the present invention; and an endoscope having the suction device that can be inserted into the lumen.

The ligature and suture system of the invention for medical application enables biomedical tissue that is being ligatured or sutured to be verified using an endoscope that has been inserted inside a lumen. In addition, after biomedical tissue has been suctioned by a suctioning device provided in the endoscope, the biomedical tissue can be ligatured or sutured via a pledget using a suturing member, and any burying of the suturing member in the biomedical tissue can be restrained.

The present invention further provides a ligature and suture method for medical application that ligatures or sutures biomedical tissue that has been suctioned by a suction device using a suturing member, the ligature and suture method including: a suction process in which an endoscope is inserted into an insertion portion having a lumen into which the endoscope can be inserted, and a distal end portion that is connected to the lumen and in which at least one side aperture is provided, and the biomedical tissue is suctioned from the side aperture into the distal end portion; an insertion process in which at least one hollow needle that is able to support inside itself the suturing member, and that is placed inside the insertion portion such that a tip of the hollow needle is able to at least move between a first position, which is on a base end side of the side aperture, and a second position, which is on a distal end side of the side aperture is inserted into the biomedical tissue and into at least one pledget that is placed between the distal end of the side aperture and the second position on a movement path of the needle so as to be freely removable from the distal end portion; a process in which the suturing member is pushed out from inside the needle to the distal side of the pledget; and a process in which suturing or ligaturing is performed using the suturing member by withdrawing the needle from the biomedical tissue.

In the ligature and suture method of the invention for medical application, after the biomedical tissue has been suctioned into the distal end portion by the suction device, the needle is inserted through both the biomedical tissue and the pledget, and these are sutured or ligatured by a suturing member. Therefore, it is possible to suppress any burying of the suturing member in the biomedical tissue.

According to the present invention, using this ligature and suture device for medical application, it is possible to cause biomedical tissue to bulge to a desired height, and a ligaturing or suturing condition can be maintained for a longer time than is the case conventionally.

BRIEF DESCRIPTION OF THE DRAWINGS

FIG. 23 is a schematic view showing the overall ligature and suture system for medical application according to the seventh embodiment of the present invention.

FIG. 38A is an explanatory view showing processing by the ligature and suture system for medical application according to the ninth embodiment of the present invention, while

FIG. 49A is a cross-sectional view taken along a line B-B in FIG. 47, while

DETAILED DESCRIPTION OF THE INVENTION

The first embodiment of the present invention will now be described with reference to FIGS. 1 through 10.

A ligature and suture system for medical application 1 according to the present embodiment is provided with an endoscope 2 and a ligature and suture device for medical application 3.

Figure 1:
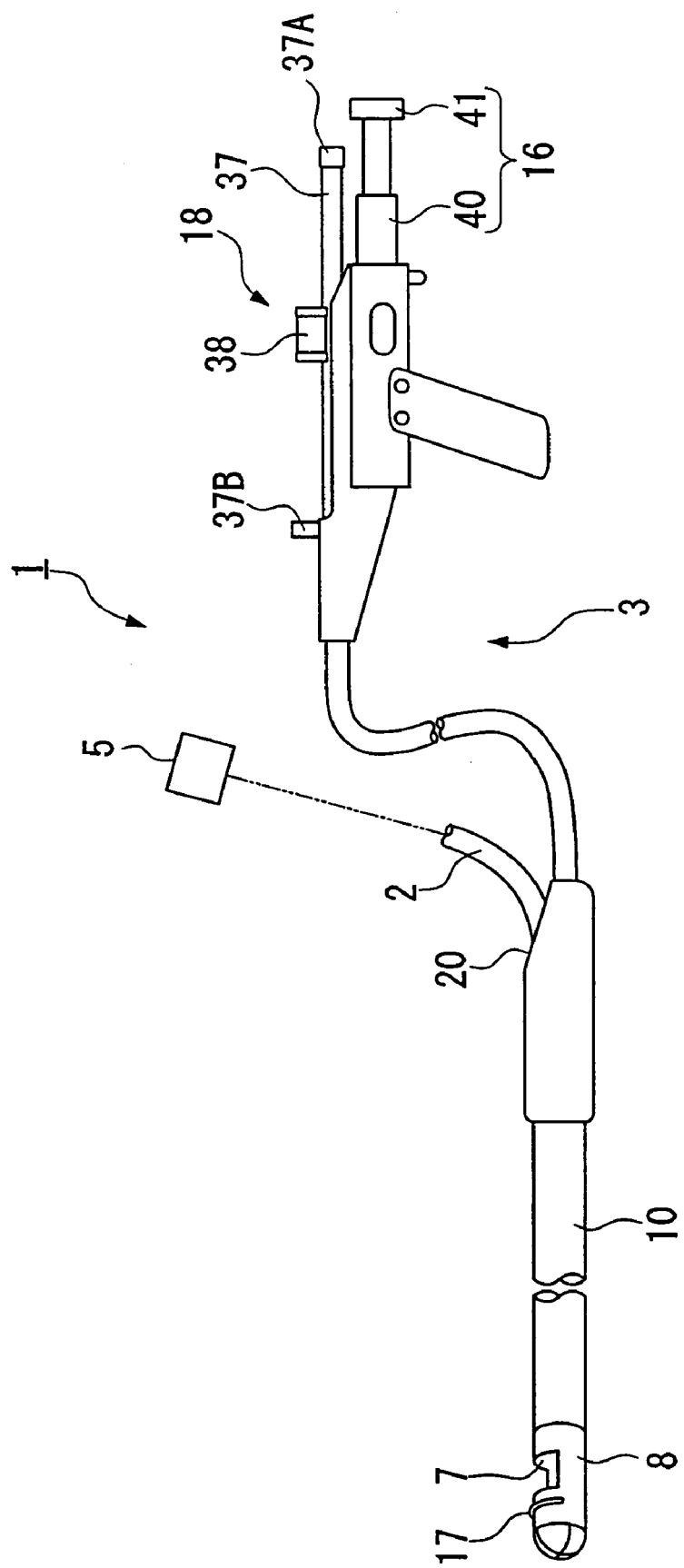
FIG. 1 is a schematic view showing a ligature and suture system for medical application according to a first embodiment of the present invention.

As shown in FIG. 1, the endoscope 2 is connected on a base end side thereof to a suction pump (i.e., a suction device) 5 and is able to suction up biomedical tissue and the like.

Figure 2:
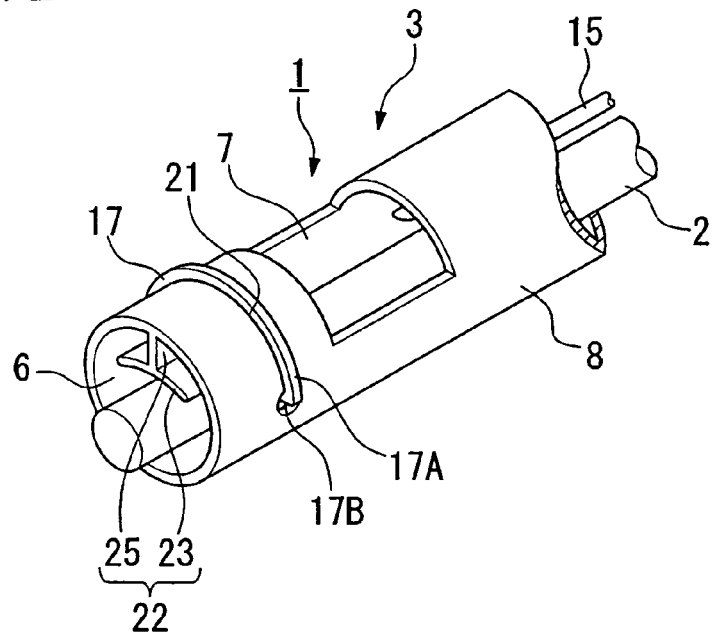
FIG. 2 is a perspective view showing a distal end portion of the ligature and suture system for medical application according to a first embodiment of the present invention.

As shown in FIG. 1 and FIG. 2, the ligature and suture device for medical application 3 is provided with an overtube (i.e., an insertion portion) 10 that has a lumen 6 into which a distal end side of the endoscope 2 can be inserted, and a distal end 8 in which a side aperture 7 is provided and that is connected to the lumen 6. The ligature and suture device for medical application 3 is also provided with two hollow needles 15 that are placed parallel with each other inside the overtube 10 so as to be able to move between a first position 11 (described below), which is on the base end side of the side aperture 7, and a second position 12 (described below), which is on the distal end side of the side aperture 7, and that are able to support inside themselves a suture member 13 (described below). The ligature and suture device for medical application 3 is also provided with an operation section 16 that performs a simultaneous movement operation on the two needles 15, one pledget 17 that is placed in the vicinity of the distal end of the side aperture 7 so as to be freely removable from the distal end portion 8 and into which the needles 15 can be inserted, and a ligature tool 18 that ligatures both tissue and the pledget 17 using the suture member 13.

The overtube 10 may be formed, for example, from a plastic material such as soft polyurethane, and is formed in a tube shape having flexibility such that it can be bent when the endoscope 2 is inserted therein. A scope insertion aperture 20 that allows the endoscope 2 to be inserted the lumen 6 is provided in base end side of the overtube 10.

The pledget 17 may be formed, for example, from polytetrafluoroethylene in a semicircular configuration, and is provided with a circular arc portion 17A that has a larger diameter than that of the distal end portion 8 and a rectilinear portion 17B that faces the circular arc portion 17A.

Figure 3:
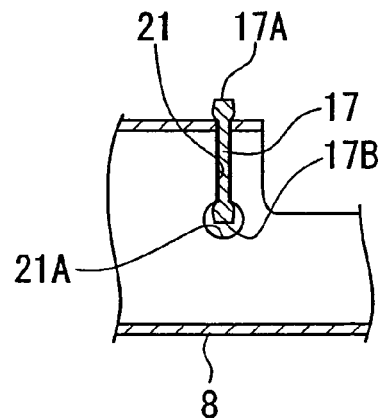
FIG. 3 is a partial enlarged showing a state in which a pledget is installed showing the ligature and suture system for medical application according to a first embodiment of the present invention.

As shown in FIG. 3, a slit 21 into which the pledget 17 can be press-inserted from the rectilinear portion 17B side is opened in a side surface of the distal end portion 8 on the distal end side of the of the side aperture portion 7. The slit 21 is formed having a depth such that, when the pledget 17 is press inserted into the slit 21, the pledget 17 lies on the movement path of the needles 15.

An enlarged portion 21 A whose width is wider than the width of the slit 21 is formed at an end of the slit 21 in order to simplify removal of the pledget 17 when the pledget 17 is being removed.

A restricting member 22 is formed on an internal circumferential surface of the distal end portion 8. The restricting member 22 restricts contact between the endoscope 2 and pledget 17 by serving as a protective member that protects the placement state such that the endoscope 2 does not strike against a pledget 17 that has been placed in the slit 21 when the endoscope 2 that has been inserted in the lumen 6 is being operated.

The restricting member 22 is placed on an internal circumferential surface of the distal end portion 8 on the distal end side of the slit 21. The restricting member 22 is provided with a pressing plate portion 23 in the shape of a curved plate that is located at substantially the same position as the rectilinear portion 17B of the pledget 17 when the pledget 17 is fitted in the slit 21. The restricting member 22 is also provided with a supporting member 25 that protrudes inwards in a radial direction from the internal circumferential surface of the distal end portion 8 and is connected with the pressing plate 23 so as to support the pressing plate 23. The base end side of the supporting portion 25 is formed so as to taper towards the distal end side so that the distal end of the endoscope 2 does not become caught even if the endoscope 2 touches the base end side of the supporting portion 25 as it is being inserted into the lumen 6.

Figure 4:
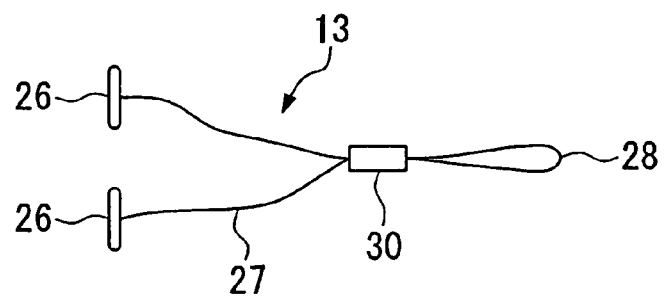
FIG. 4 is an overall view showing a suturing member of the ligature and suture system for medical application according to a first embodiment of the present invention.

As shown in FIG. 4, the suture member 13 is provided with bar shaped T-bars 26 that can be inserted inside the needles 15, a thread 27 that is connected at both ends to the T-bars 26, and a stopper 30 that is formed from silicon resin or the like and that is placed between the T-bars 26 and a loop portion 28, which is formed by folding the thread 27 back into two strands, so as to be able to slide along the thread 27.

Figure 5:
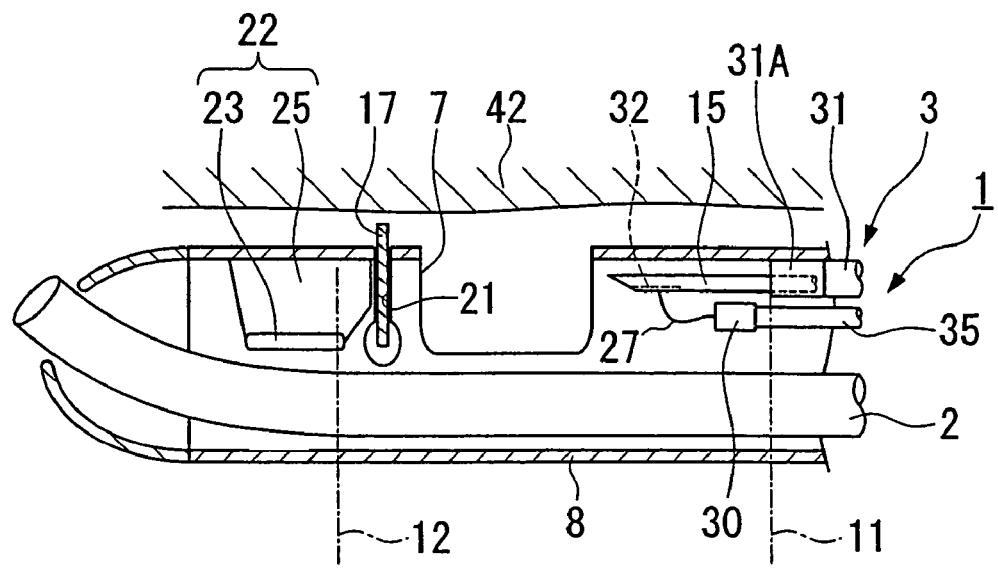
FIG. 5 is an enlarged view of the principal portions showing the ligature and suture system for medical application according to a first embodiment of the present invention.

As shown in FIG. 5, the needles 15 are both placed inside a needle lumen 31 located inside the overtube 10 such that they can be moved forwards or backwards. A distal end of the needle lumen 31 is fixed to an internal wall of the overtube 10 as a base end side needle guide portion 31A.

A needle slit 32 is formed in a distal end of the needles 15. When the T-bars 26 are supported inside the needles 15, the thread 27 passes through the needle slit 32 from a side surface of the needles 15 towards the outside. A pushing member (not shown), which pushes the T-bars 26 that have been mounted inside the needles 15 outwards from the distal ends of the needles 15, is provided in the needles 15 so as to be able to move forwards and backwards relative to the needles 15.

Note that the first position 11 is the base end side needle guide portion 31A, and the second position 12 is a position on the distal end side of the slit 21.

The ligature tool 18 is provided with a ligature sheath 35 that is placed so as to be able to move forwards and backwards inside the lumen 6 and is connected to the base end of the stopper 30 and pushes the stopper 30 towards the T-bars 26, a ligature wire (not shown) that is able to be moved backwards and forwards inside the ligature sheath 35 and that grips the loop portion 28 of the thread 27, a ligature tool operating member 37 that is connected to a base end of the ligature sheath 35 and moves the ligature sheath 35 backwards and forwards inside the lumen 6, and a ligature handle 38 that is connected to a base end of the ligature wire and moves the ligature wire backwards and forwards inside the ligature sheath 35.

The ligature tool operating member 37 is provided with a first finger piece portion 37A that is positioned at the base end and a second finger piece portion 37B that is positioned a predetermined distance apart from the first finger piece portion 37A. The ligature handle 38 can be moved backwards and forwards between the first finger piece portion 37A and the second finger piece portion 37B.

The operation section 16 is provided with a needle handle 40 that is connected to the base end of the needles 15 and that moves the needles 15 backwards and forwards inside the needle lumen 31, and a pusher handle 41 that is connected to a base end of the pushing member and that moves the pushing member backwards and forwards inside the needles 15.

The needle handle 40, the pusher handle 41, and the ligature tool operating member 37 are all able to move such that the distal ends of the needles 15 are able to reach the second position 12. Thereafter, the pusher handle 41 and the ligature tool operating member 37 can be moved further towards the distal end side.

Next description of a method of using the ligature and suture device for medical application 1 and the ligature and suture system for medical application 3 according to the present embodiment, as well as the actions and effects thereof will be given.

Figure 6:
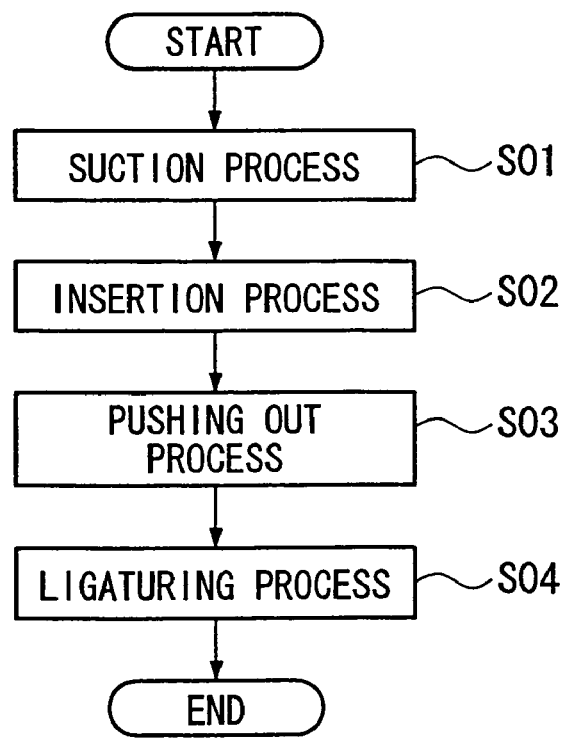
FIG. 6 is a flow chart showing the ligature and suture method for medical application according to a first embodiment of the present invention.

As shown in FIG. 6, the ligaturing of biomedical tissue involves a suction process (S01), an insertion process (S02), a pushing out process (S03), and a ligaturing process (S04).

Firstly, the suction process (S01) is performed.

In this process, the endoscope 2 is inserted from the scope insertion aperture 20, and the overtube 10 is then inserted into the body of a patient with the endoscope 2 protruding from the distal end portion 8. As shown in FIG. 5, an operator then moves the distal end portion 8 to the vicinity of the biomedical tissue 42 while verifying the movement on an endoscope image.

Next, the distal end of the endoscope 2 is drawn back to the base end side of the side aperture 7, and the operator rotates the overtube 10 or moves it backwards or forwards while confirming the movement on the endoscope image, thereby positioning the side aperture 7 at a position facing the biomedical tissue 42. At this time, even if the distal end of the endoscope 2 is moved backwards or forwards relative to the distal end portion 8, because the endoscope 2 and the pledget 17 do not make contact with each other due to the restricting member 22, or if they do make contact with each other, because the pledget 17 maintains its initial installation condition, the pledget 17 is placed in a state in which it is reliably held in the slit 21.

Figure 7A:
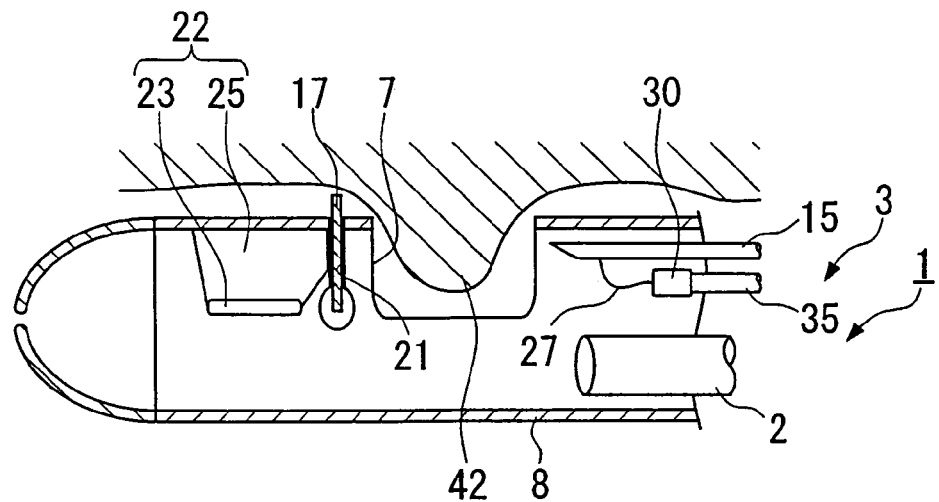
FIGS. 7A and 7B are explanatory views showing a treatment using the ligature and suture system for medical application according to a first embodiment of the present invention.

In this state, the suction pump 5 is operated so that, as shown in FIG. 7A, the biomedical tissue 42 is suctioned from the side aperture 7 into the distal end portion 8. At this time, it is confirmed as to whether or not the target puncture site is positioned on the movement path of the needles 15.

After the positioning, the routine moves to the insertion process (S02).

Namely, the push handle 41 is pushed to the distal end side. At this time, both the push handle 40 and the ligature tool operating member 37 move to the distal end side, and the needles 15 are each pushed out to the distal end side relative to the needle lumen 31, and the ligature tool 18 moves to the distal end side together with the needles 15. The biomedical tissue 42 and the pledget 17 are then both punctured by the needles 15.

Next, a process to push the suture member 13 out from inside the needles 15 to the distal side of the pledget 17 is performed (S03).

Figure 7B:
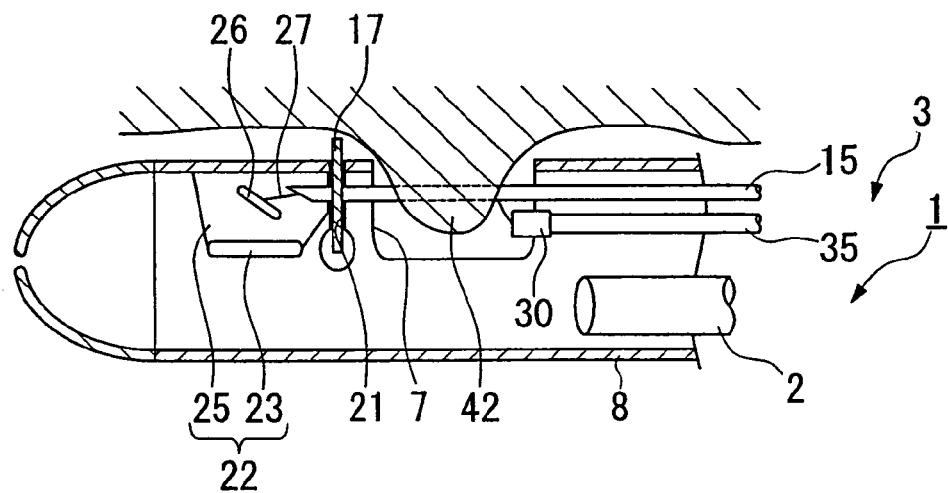

Namely, by further pushing out the push handle 41 when the distal ends of the needles 15 reach the second position, the pushing member moves towards the distal end side relative to the needles 15. At this time, as shown in FIG. 7B, the T-bars 26 inside the needles 15 are pushed to the distal side of the pledget 17.

The routine then moves to the ligature process (S04).

When the push handle 41 is drawn back to the base end side, the pushing member is withdrawn into the needles 15.

Figure 8A:
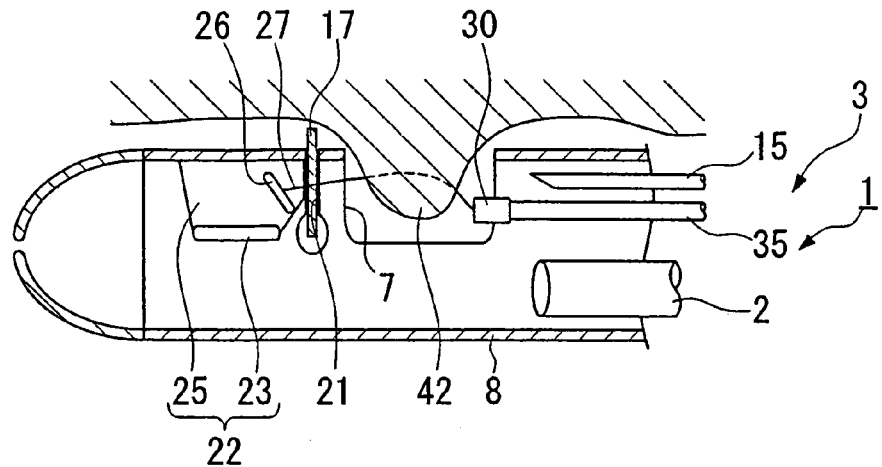
FIGS. 8A to 8C are explanatory views showing a treatment using the ligature and suture system for medical application according to a first embodiment of the present invention.

Furthermore, when the push handle 41 is drawn back, the needle handle 40 moves in connection with this, and the needles 15 are moved to the first position 11. At this time, the thread 27 is withdrawn from inside the needles 15 via the needle slit 32, and, as shown in FIG. 8A, the thread 27 is placed in a state of insertion through the biomedical tissue 42.

Figure 8B:
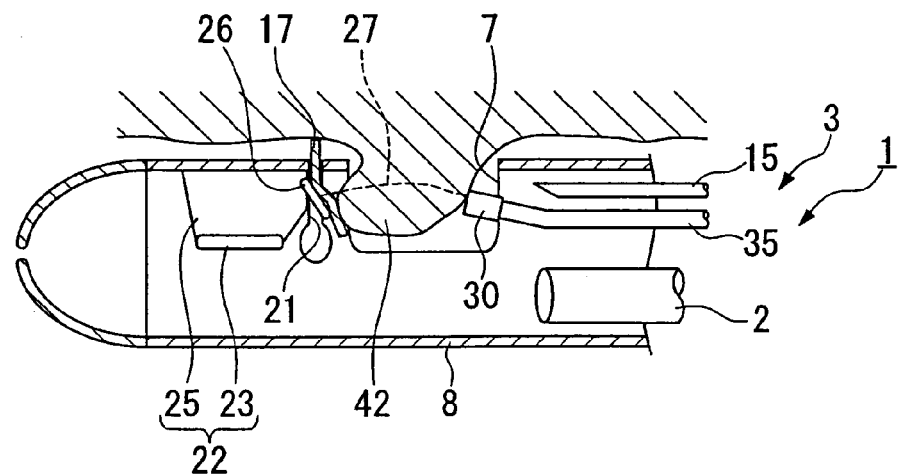

Next, the ligature handle 38 is moved relative to the ligature tool operating member 37 from the second finger piece portion 37B in the direction of the first finger piece portion 37A. At this time, because the thread 27 is drawn back while the stopper 30 is being pushed back by the ligature sheath 35, as shown in FIG. 8B, the biomedical tissue 42 is tightened with the T-bar 26 being in this state of pressure contact against the pledget 17.

Figure 8C:
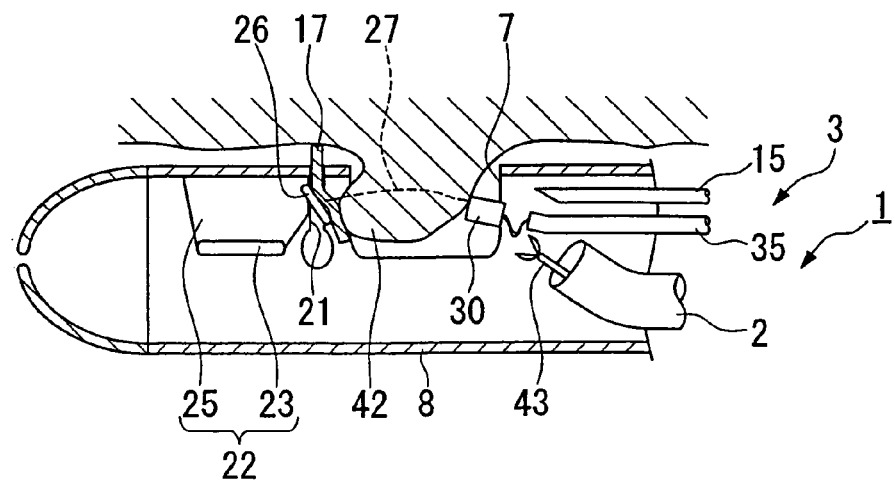
Figure 9A:
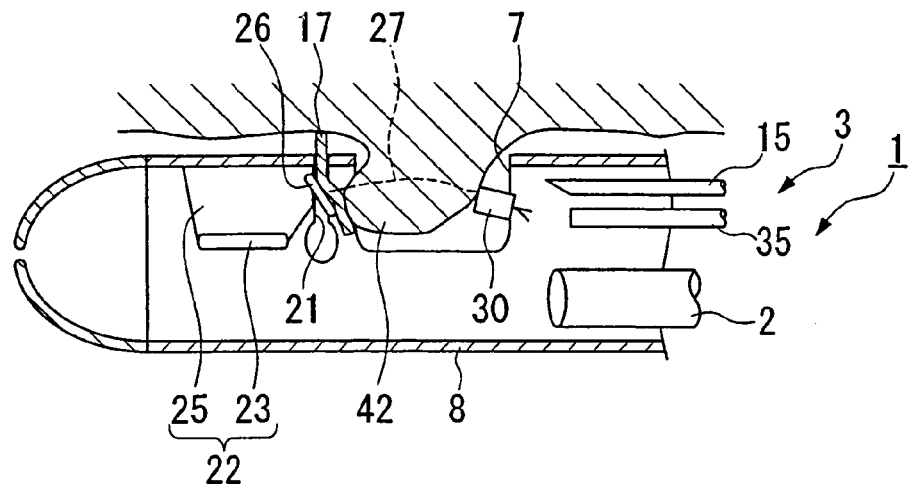
FIGS. 9A to 9C are explanatory views showing a treatment using the ligature and suture system for medical application according to a first embodiment of the present invention.

As shown in FIG. 8C, forceps 43 that have been inserted in a channel in the endoscope 2 are made to protrude from the distal end of the endoscope 2 and, as shown in FIG. 9A, cut the thread 27.

Figure 9B:
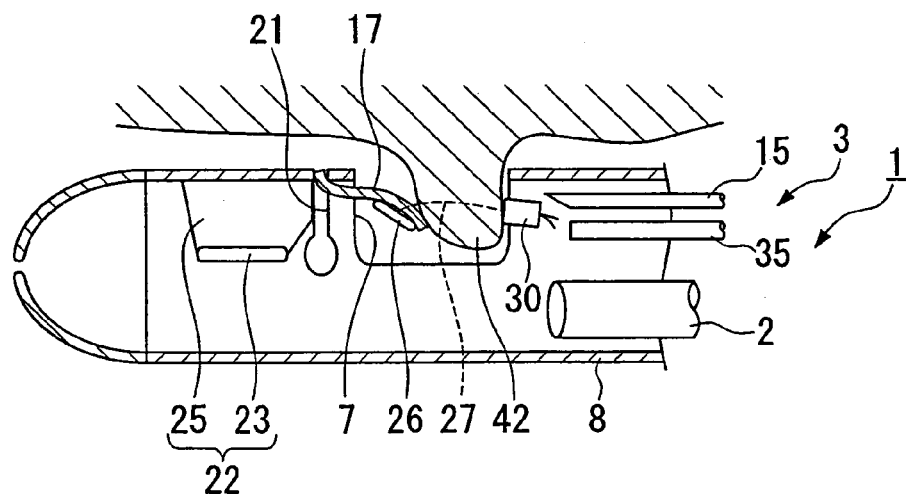
Figure 9C:
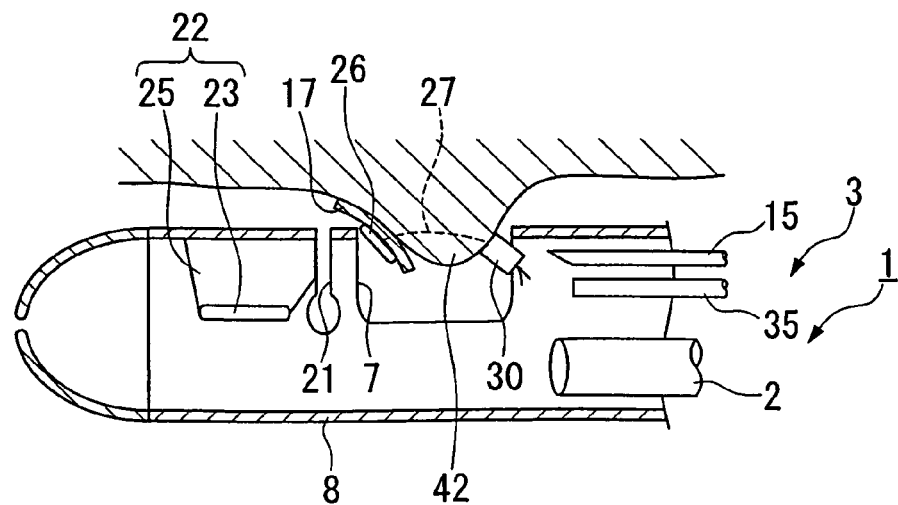

At this time, as shown in FIG. 9B, as a result of the pledget 17 becoming separated from the slit 21 from the rectilinear portion 17B side, and the distal end portion 8 also moving away from the biomedical tissue 42, as shown in FIG. 9C, the biomedical tissue 42 is removed from the side aperture 7.

Figure 10:
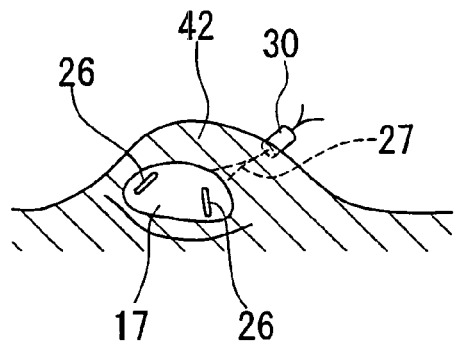
FIG. 10 is an explanatory view showing results of a treatment using the ligature and suture system for medical application according to a first embodiment of the present invention.

In this manner, as shown in FIG. 10, the biomedical tissue 42 is ligatured in a bulging state together with the pledget 17.

According to this ligature and suture device for medical applications 3 and the ligature and suture system for medical applications 1, it is possible to place the pledget 17 between the T-bars 26 and the biomedical tissue 42, and the T-bars 26 can be prevented from becoming buried in the biomedical tissue 42. Accordingly, the biomedical tissue 42 can be made to bulge out to the desired height, and the ligature condition can be maintained for a longer time than is possible conventionally.

Moreover, before and after the endoscope 2 is operated, it is possible using the restricting member 22 to prevent the endoscope 2 from colliding against the pledget 17 and from moving or deforming the pledget 17 inside the distal end portion 8. Any shift between the pledget 17 and the movement part of the needles 15 is suppressed, and the needles 15 can be made to penetrate better.

At this time, because the restricting member 22 is placed in the vicinity of the pledget 17, the pledget 17 can be prevented from escaping to the distal side even when the needles 15 pierce the pledget 17, so that the initial installation condition can be maintained, and a more excellent puncture state can be maintained.

Furthermore, by press-inserting the pledget 17 into the slit 21, the pledget 17 can be aligned in a direction that is orthogonal to the movement path of the needles 15, so that the pledget 17 can be reliably pierced by the needles 15. Moreover, by pulling the pledget 17 from the inner side in the radial direction of the distal end portion 8, the pledget 17 can be easily removed from the distal end portion 8.

Figure 11A:
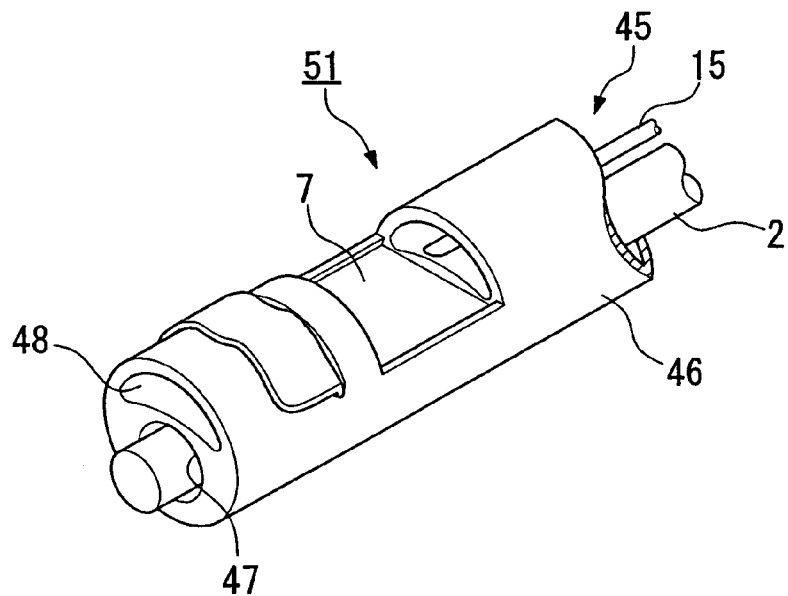
FIG. 11A is a perspective view and FIG. 11B is a cross-sectional view showing a distal end portion of a ligature and suture system for medical application according to a second embodiment of the present invention.
Figure 11B:
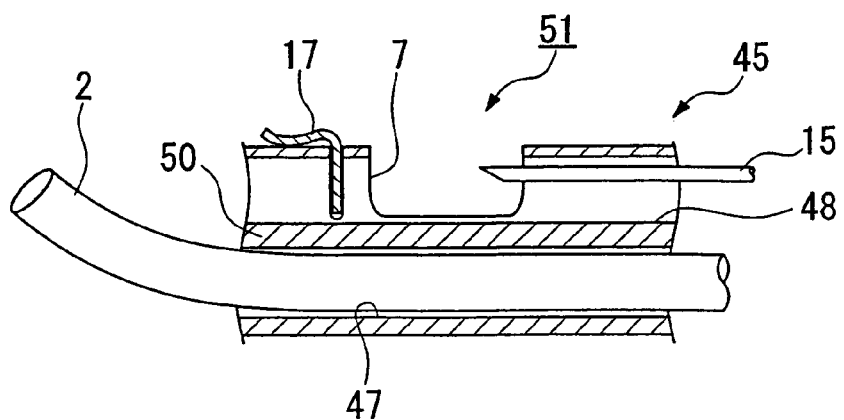

Next, the second embodiment will be described with reference to FIGS. 11A and 11B.

Note that the same symbols are allocated to the same component elements as those in the above described first embodiment, and a description thereof is omitted.

The second embodiment differs from the first embodiment in that the restricting member that is positioned at a distal end portion 46 of the ligature and suture device for medical application 45 according to the present embodiment forms of partitioning member 50 that partitions a first lumen 47 into which the endoscope 2 can be inserted from a second lumen 48 into which the needles 15 and the ligature tool 18 can be inserted.

The side aperture 7 is provided in a side surface on the second lumen 48 side, and the slit 21 is also provided so as to extend from the side surface on the side aperture 7 side to the partitioning member 50. The pledget 17 is able to be inserted so as to shield the second lumen 48 partway along, and when the pledget 17 is larger than the size of the second lumen 48, during insertion the circular arc portion 17A side is made to stick out from the slit 21 and is then folded back onto the distal end side and then insertion is made.

When this ligature and suture device for medical application 45 and the ligature and suture system for medical application 51 are used, because it is not possible to use the suction pump 5 of the endoscope 2, another suction device (not shown) is connected to the second lumen 48 and the suction process is performed (S02).

According to this ligature and suture device for medical application 45 and the ligature and suture system for medical application 51, the same actions and effects can be obtained as from the first embodiment, however, because the partitioning member 50 is provided, it is possible to reliably prevent contact between the endoscope 2 and the pledget 17, even when the endoscope 2 is operated inside the distal end portion 46.

Figure 12A:
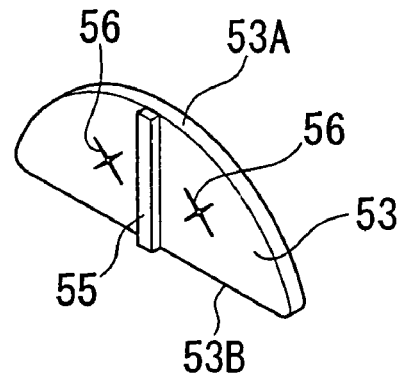
FIG. 12A is a perspective view and FIG. 12B is a front view showing a pledget of a ligature and suture system for medical application according to a third embodiment of the present invention.
Figure 12B:
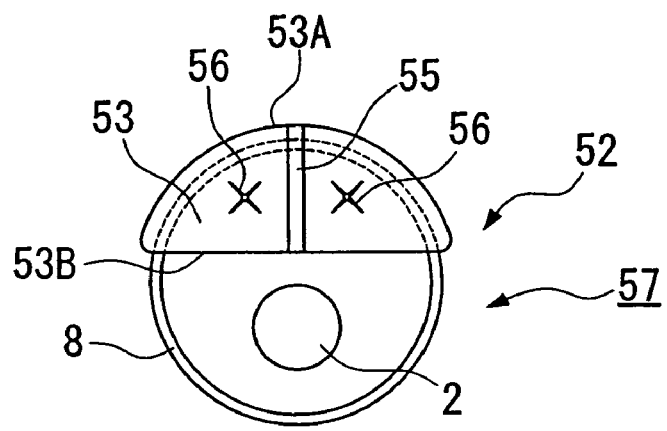

Next, the third embodiment will be described with reference to FIGS. 12A and 12B.

Note that the same symbols are allocated to the same component elements as those in the above described embodiments, and a description thereof is omitted.

The third embodiment differs from the first embodiment in that, in the ligature and suture device for medical application 52 according to the present embodiment, instead of the restricting member, a rib (i.e., a protective member) 55 that reinforces the pledget 53 itself is provided in the pledget 53.

The rib 55 is formed in a rectilinear shape in the center portion of the pledget 53 extending from a circular arc portion 53A to a rectilinear portion 53B and is thicker than the thickness of the pledget 53.

Notches 56 are also formed in the pledget 53 at positions that are on the respective paths of movement of the needles 15 when the pledget 53 is fitted into the slit 21.

According to this ligature and suture device for medical application 52 and the ligature and suture system for medical application 57, even if the distal end side of the endoscope 2 comes into contact with the pledget 53, it is possible using to the rib 55 to suppress deformation of the pledget 53 itself which may cause it to come loose from the slit 12. Moreover, any shift in the pledget 53 in a sideways direction relative to the slit 21 can be prevented and the installation condition of the pledget 53 can be maintained.

Next, the fourth embodiment will be described with reference to FIGS. 13 through 16C.

Note that the same symbols are allocated to the same component elements as those in the above described embodiments, and a description thereof is omitted.

The fourth embodiment differs from the first embodiment in that the ligature and suture device for medical application 60 according to the present embodiment is provided with distal end side needle guide portions 62 that guide the distal ends of the needles 15 to a pledget 61.

Figure 13:
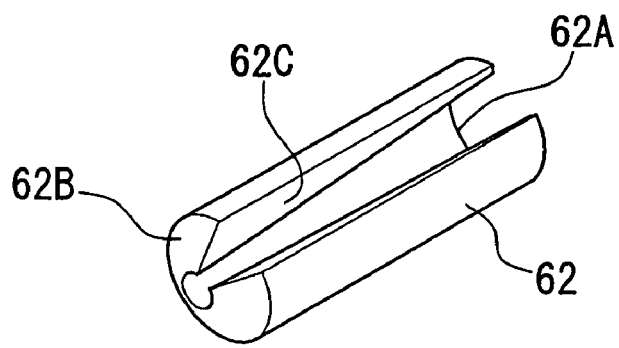
FIG. 13 is a perspective view showing a distal end side needle guide portion of a ligature and suture device for medical application according to a fourth embodiment of the present invention.

As shown in FIG. 13, each distal end side needle guide portion 62 is formed as a circular cylinder whose internal diameter becomes gradually narrower moving from a base end 62A on the side of the operator towards a distal end 62B on the pledget side, and the inner diameter at the other end 62B is formed having substantially the same size as the outer diameter of the needles 15.

A needle guide slit 62C is formed at a portion of the outer circumferential surface of the distal end side needle guide portions 62 having a width that is less than the outer diameters of the needles 15 and is greater than the diameter of the thread 27.

Figure 14:
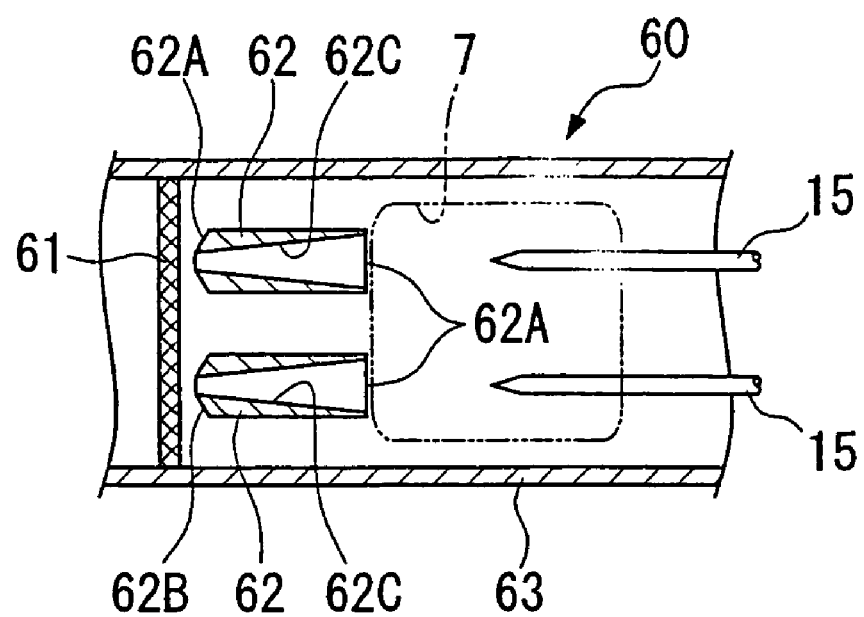
FIG. 14 is a partial enlarged showing a ligature and suture system for medical application according to a fourth embodiment of the present invention.

As shown in FIG. 14, the distal end side needle guide portions 62 are positioned on the distal end side of the side aperture 7 in a distal end portion 63 that is on the movement path of each of the needles 15 and on the base end side of the pledget 61, and are positioned such that the base end 62A sides that are on the side of the operator are on the side of the side aperture 7.

Figure 15:
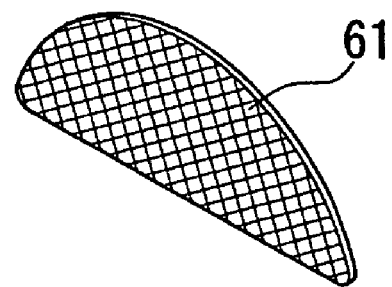
FIG. 15 is a perspective view showing a pledget of the ligature and suture device for medical application according to a fourth embodiment of the present invention.

As shown in FIG. 15, the pledget 61 is formed as a mesh in order to allow the needles 15 to pass through easily.

Next, a description of a method of using the ligature and suture system for medical application 65 and the ligature and suture device for medical application 60 according to the present embodiment, as well as the actions and effects thereof will be given.

Firstly, as shown in FIG. 14, the distal end side needle guide portion 62 is placed in the distal end portion 63.

Figure 16A:
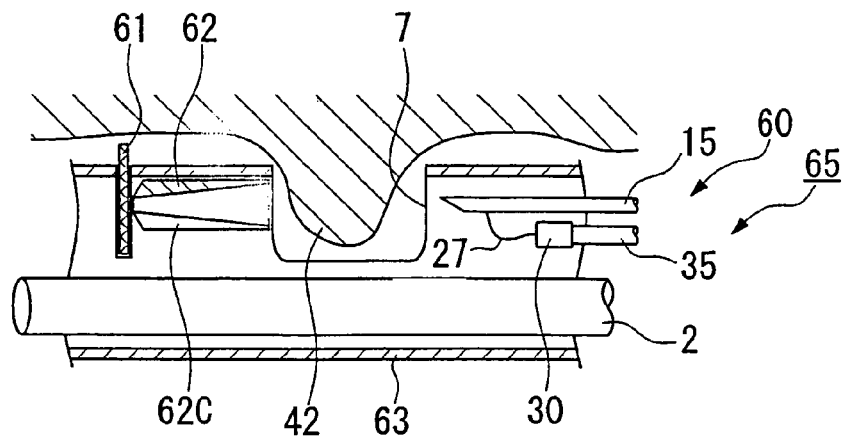
FIGS. 16A to 16C are explanatory views showing a treatment using the ligature and suture system for medical application according to a fourth embodiment of the present invention.

Next, in the same way as in the first embodiment, a suction process (S01) is conducted, and, as shown in FIG. 16A, the biomedical tissue 42 is drawn inside the side aperture 7.

The routine then moves to an insertion process (S02).

The pusher handle 41 is pushed in towards the distal end side so that the needles 15 are pushed out respectively on the distal end side relative to the needle lumen 31, and the biomedical tissue 42 and the pledget 61 are pierced by the needles 15.

At this time, after piercing the biomedical tissue 42, the needles 15 are both inserted from the base ends 62A, which are on the side of the operator, of the distal end side needle guide portion 62 into the interior thereof, and then protrude from the distal ends 62B that are on the pledget side, and are inserted into the mesh of the pledget 61.

Figure 16B:
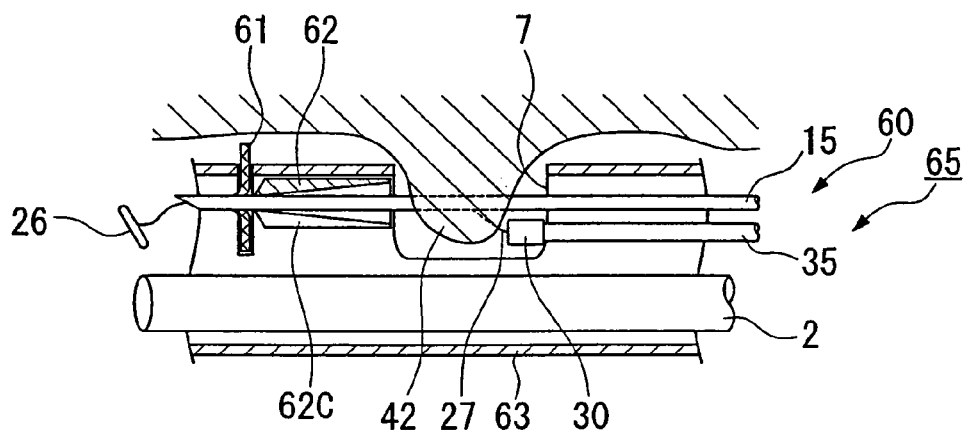

When the distal ends of the needles 15 reach the second position 12, the routine moves to a pushing out process (S03) and the pusher handle 41 is pushed out further. As a result, the pushing member is moved to the distal end side relative to the needles 15, and, as shown in FIG. 16B, the T-bars 26 inside the needles 15 are pushed to the distal side of the pledget 16.

The routine then moves to the ligaturing process (S04).

The pusher handle 41 is pulled to the base end side, and the pushing member is withdrawn inside the needles 15.

Furthermore, if the pusher handle 41 is pulled in until the needles 15 are made to arrive at the first position 11, then the thread 27 is pulled out from inside the needles 15 via the needle slit 32.

Figure 16C:
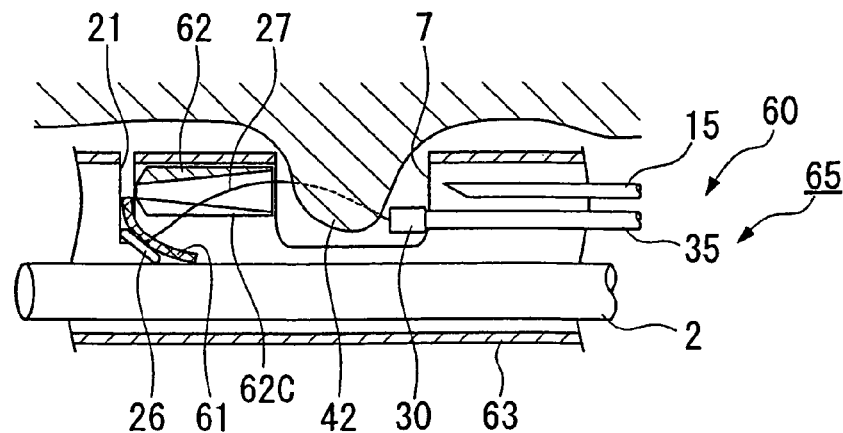

At this time, as shown in FIG. 16C, the pledget 61 is withdrawn from the slit 21, and after the thread 27 has been withdrawn from the needle guide slits 62, the ligature process continues in the same way as in the first embodiment.

According to this ligature and suture system for medical application 65 and the ligature and suture device for medical application 60 of the present embodiment, by inserting the needles 15 along the distal end side needle guide portion 62, it is possible to reliably guide the needle points to the pledget 61, and the piercing accuracy can be improved.

Next, the fifth embodiment will be described with reference to FIGS. 17A through 19.

Note that the same symbols are allocated to the same component elements as those in the above described embodiments, and a description thereof is omitted.

The fifth embodiment differs from the fourth embodiment in that a reinforcing portion 75 that increases the rigidity of a distal end portion 71 is placed between the first position 11 and the second position 12 of the distal end portion 71 of a ligature and suture device for medical application 70 according to the present embodiment.

Figure 17A:
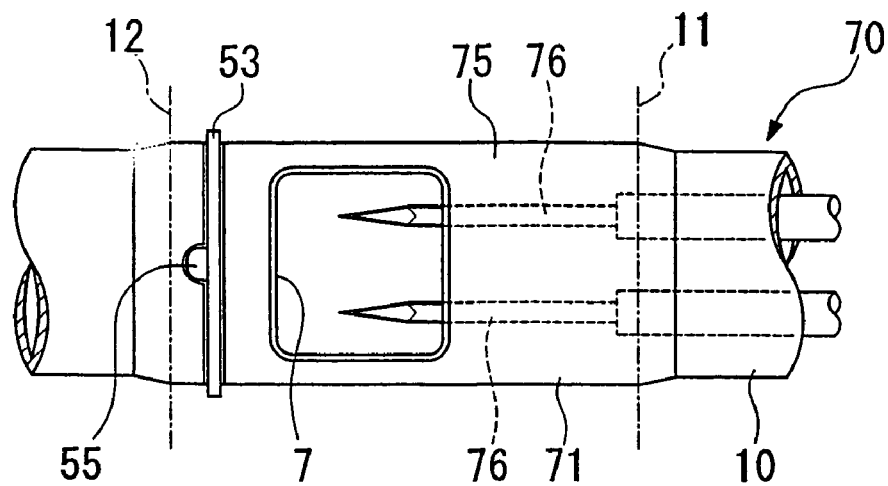
FIG. 17A is a frontal enlarged view and FIG. 17B is a side surface cross-sectional view showing principal portions of a ligature and suture system for medical application according to a fifth embodiment of the present invention.
Figure 17B:
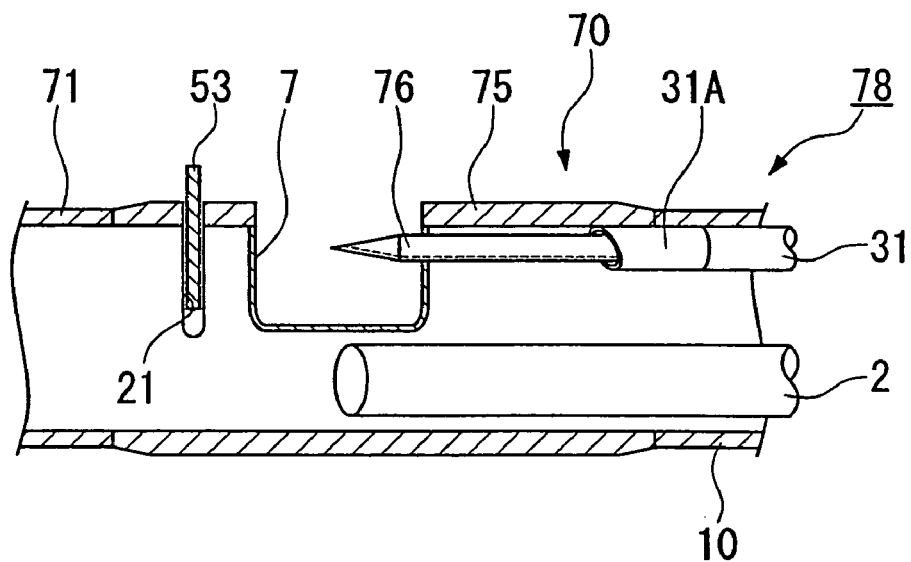

As shown in FIGS. 17A and 17B, the reinforcing portion 75 is formed having a larger thickness than other portions of the overtube 10 and distal end portion 71 in order to fix an area from a needle fixed position (i.e., a base end side needle guide portion 31A) to a needle point arrival position (i.e., the pledget 53) as one body. Note that the pledget here is the pledget 53 according to the third embodiment, however, the pledgets according to the other embodiments may also be used. In addition, in the present embodiment, the distal side position of the reinforcing portion 75 is the second position 12, however, if the distal end side needle guide portion 62 is provided, the distal side position of the reinforcing portion 75 may extend to the distal end side needle guide portion 62.

Figure 18A:
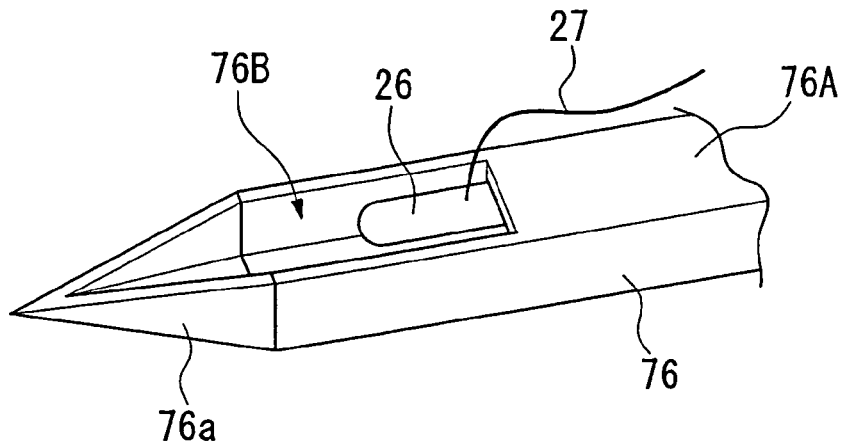
FIG. 18A is a perspective view showing a distal end of a needle.
Figure 18B:
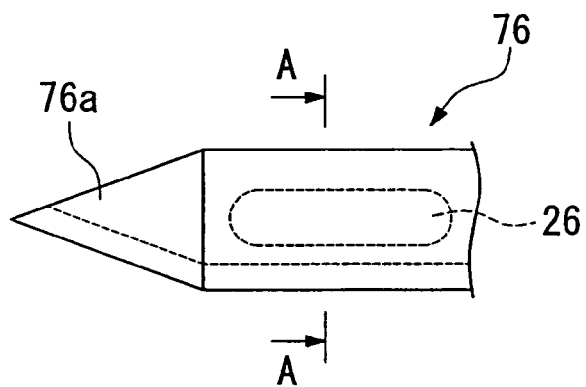
FIG. 18B is a side surface view showing a distal end of a needle.
Figure 18C:
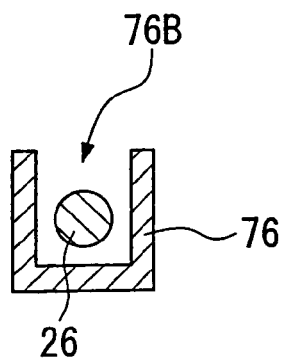
FIG. 18C is a cross-sectional view taken along a line A-A in FIG. 18B of the ligature and suture device for medical application according to a fifth embodiment of the present invention.
Figure 19:
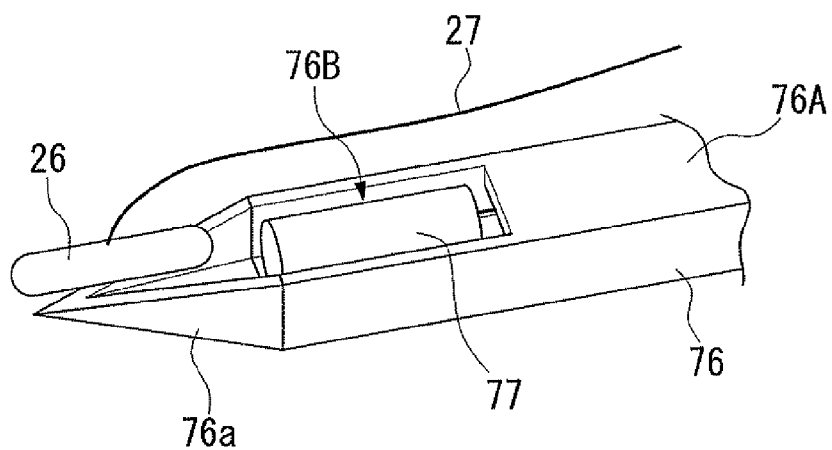
FIG. 19 is an explanatory view showing a state in which a T-bar is discharged from the distal end of a needle of the ligature and suture device for medical application according to the fifth embodiment of the present invention.
Figure 20:
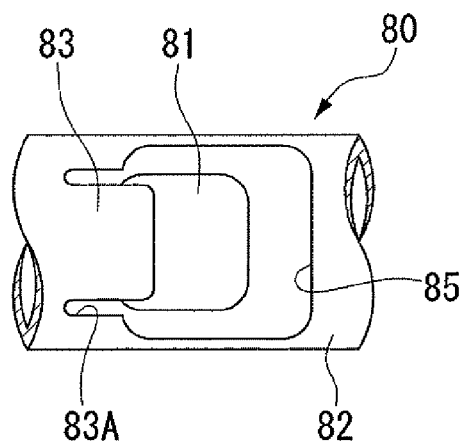
FIG. 20 is a partial enlarged showing a ligature and suture device for medical application according to a sixth embodiment of the present invention.

As shown in FIGS. 18A, 18B, and 18C, the needles 76 are formed such that the cross-sectional configuration thereof is a square configuration, and a distal end 7 thereof is tapered. Moreover, an aperture portion 76B, via which a T-bar 26 can be inserted and removed, is formed in one side surface 76A of the distal end 76a. Accordingly, when the T-bars 26 are pushed out by the pushing member 77, the T-bar 26 can be slid out from the aperture portion 76B.

According to this ligature and suture device for medical application 70 and the ligature and suture system for medical application 78, the positional relationship between the needles 76, the side aperture 7, and the pledget 53 can be maintained by the reinforcing portion 75. In addition, any wavering of the needles 76 can be suppressed at the moment of piercing, and they can be reliably guided to the pledget 53 so as to pierce the pledget 53. At this time, because the needles 76 are formed in a square configuration, if the distal end portion 71 is deformed, the rigidity thereof can be increased compared with when the needles have a circular cylindrical configuration. Furthermore, because the distal ends 7 are in the center of the needles 76, the stability of the straight advancement of the needles can be increased, and any wavering of the needles can be further suppressed.

Next, the sixth embodiment will be described with reference to FIGS. 20, 21A, 21B, and 21C.

Note that the same symbols are allocated to the same component elements as those in the above described embodiments, and a description thereof is omitted.

The sixth embodiment differs from the first embodiment in that, instead of the restricting member 22 of the first embodiment, the ligature and suture device for medical application 80 according to the present embodiment is provided with a pledget support portion 83 that is provided integrally with a distal end portion 82 and supports a pledget 81, and that is able to change the pledget 81 from a direction parallel with the needles 15 to a direction in which the needles 15 can pierce the pledget 81.

The pledget support portion 83 changes the orientation of the pledget 81 when deformation force is supplied thereto by suction from the suction pump (i.e., deformation device) 5 of the endoscope 2.

The pledget support portion 83 is provided integrally with a distal end portion 82 in a portion of the distal end of a side aperture 85, and a slit 86 is formed running from the distal end of the side aperture 85 further in the direction of the distal end. As a result, when the pledget 81 is mounted in the slit 86, the pledget 81 is mounted in a direction parallel with the lumen 6. A notch portion 83A that is able to be bent from the distal end portion 82 in the radial direction of the distal end portion 82 is formed in the pledget support portion 83.

Next, a description of a method of using the ligature and suture device for medical application 80 and the ligature and suture system for medical application 87 according to the present embodiment, as well as the actions and effects thereof will be given.

Firstly, the suction process (S01) is performed.

The overtube 10 into which the endoscope 2 has been inserted is inserted into the body of a patient, and is brought closer to the vicinity of the biomedical tissue 42.

Figure 21A:
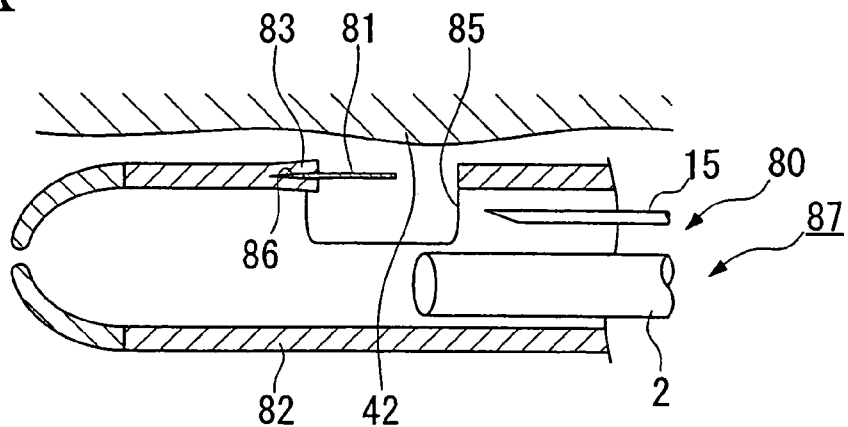
FIG. 21A is a partial enlarged view showing a ligature and suture system for medical application and FIGS. 21B and 21C are explanatory views showing a ligaturing and suturing method for medical application according to the sixth embodiment of the present invention.

Next, the distal end of the endoscope 2 is drawn back to the base end side of the side aperture 85, and the overtube 10 is rotated or moved backwards or forwards so that, as shown in FIG. 21A, the side aperture 85 is positioned at a position facing the biomedical tissue 42.

At this time, even if the distal end of the endoscope 2 is moved backwards or forwards relative to the distal end portion 82, because the pledget 81 is mounted so as to be in parallel with the distal end portion 82 due to the pledget support portion 83, contact between the endoscope 2 and the pledget 81 is restricted, and the pledget 81 is placed in a state in which it is held in the slit 86.

Figure 21B:
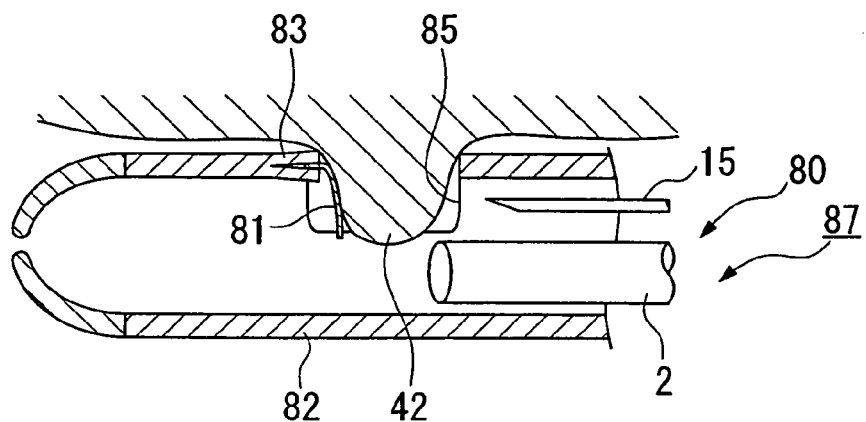

In this state, the suction pump 5 is operated so that, as shown in FIG. 21B, the biomedical tissue 42 is suctioned from the side aperture 85 into the distal end portion 82. At this time, the pledget support portion 83 is deformed by being pressed by the suctioned biomedical tissue 42, and the pledget 81 is bent inside the distal end portion 82 from the side aperture 85 to a position on the movement path of the needles 15.

Figure 21C:
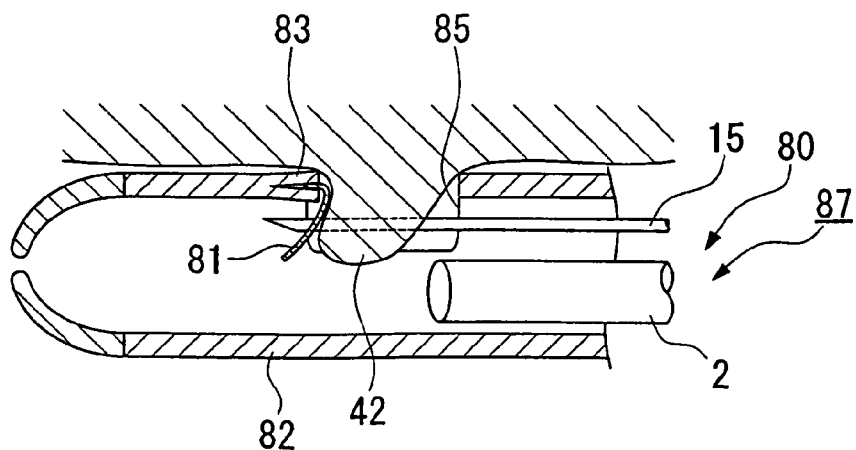

In this manner, when the routine moves to the insertion process (S02), as shown in FIG. 21C, the biomedical tissue 42 and the pledget 18 are pierced by the needles 15 and, in the same way as in the above described embodiments, the pushing out process (S03) and the ligature process (S04) are conducted.

According to this ligature and suture device for medical application 80 and the ligature and suture system for medical application 87, when the endoscope 2 is inserted into the distal end portion 82 and is moved forwards or backwards, or is rotated, it is possible to reliably suppress interference between the endoscope 2 and the pledget 81. Moreover, only when the needles 15 are inserted in the pledget 81 is the suction pump 5 operated and the pledget support portion 83 deformed, so that the orientation of the pledget 82 can be changed and the needles 15 can be inserted.

Next, the seventh embodiment will be described with reference to FIGS. 22A, 22B, and 23.

Note that the same symbols are allocated to the same component elements as those in the above described embodiments, and a description thereof is omitted.

Figure 22A:
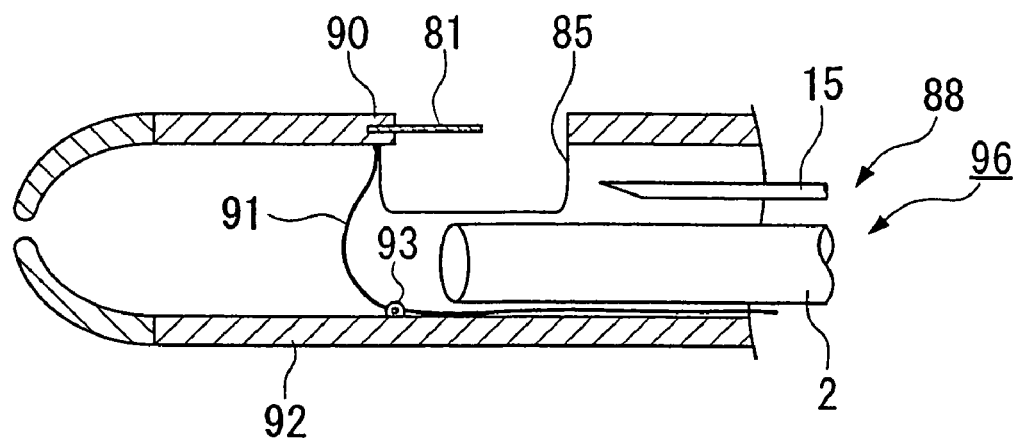
FIG. 22A is an enlarged view showing principal portions and FIG. 22B is an explanatory view showing a treatment of a ligature and suture system for medical application according to a seventh embodiment of the present invention.
Figure 22B:
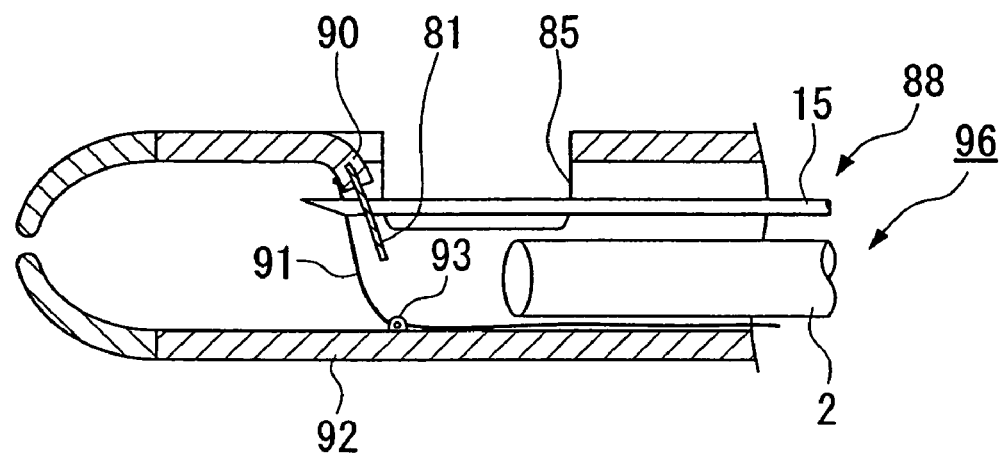

The seventh embodiment differs from the sixth embodiment in that, as shown in FIG. 22A, a distal end of a wire member 91 that has elasticity is connected as a deformation device to a pledget support portion 90 with which a ligature and suture device for medical application 88 according to the present embodiment is equipped.

A wire support portion 93 that supports the wire member 91 such that it can be freely inserted through the wire support portion 93 is placed at an inner surface of a distal end portion 92. The wire member 91 is placed so as to run along the overtube 10 and, as shown in FIG. 23, the base end thereof is connected to a pledget operating handle 95 that is placed so as to be able to move forwards or backwards on the ligature tool operating member 37.

Next, a description of a method of using the ligature and suture device for medical application 88 and the ligature and suture system for medical application 96 according to the present embodiment, as well as the actions and effects thereof will be given.

Firstly, the suction process (SO 1) is performed in the same way as in the above described sixth embodiment.

At this time, in accompaniment to the suction of the biomedical tissue 42, the pledget operating handle 95 is moved to the first finger piece portion 37A side. As a result, the wire member 91 moves to the base end side of the overtube 10, and the forwards or backwards motion force of the wire member 91 is converted by the wire supporting portion 93 into a deformation force acting on the pledget support portion 90. As a result, the pledget 81 is bent inside the distal end portion 92 from the side aperture 85 to a position that is on the movement path of the needles 15.

Subsequently, in the same way as in the above described embodiments, the insertion process (S02), the pushing out process (S03), and the ligature process (S04) are performed.

According to this ligature and suture device for medical application 88 and the ligature and suture system for medical application 96, by operating the wire member 91 at the moment of the piercing by the needles 15, the pledget support portion 90 can be deformed, and the needles 15 can be inserted into the pledget 81.

Note that the technical range of the present invention is not limited to the above described embodiments and various modifications may be made insofar as they do not depart from the scope of the present invention.

Figure 24:
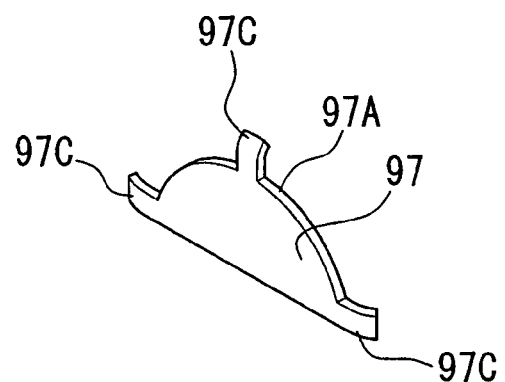
FIG. 24 is a perspective view showing a pledget of a ligature and suture device for medical application according to another embodiment of the present invention.
Figure 25A:
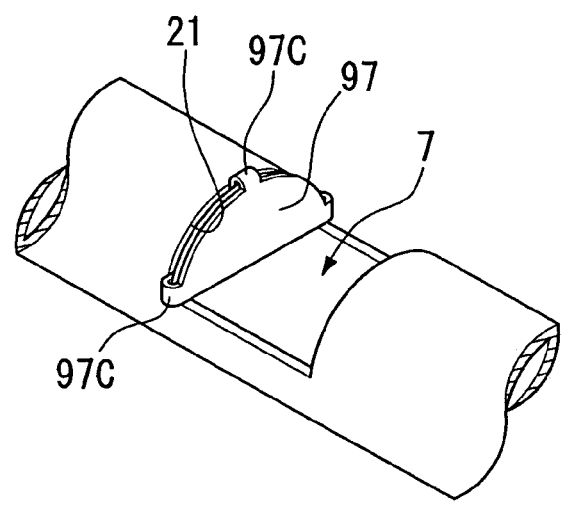
FIG. 25A is an enlarged view and FIG. 25B is a cross-sectional view showing principal portions of a ligature and suture device for medical application according to another embodiment of the present invention.
Figure 25B:
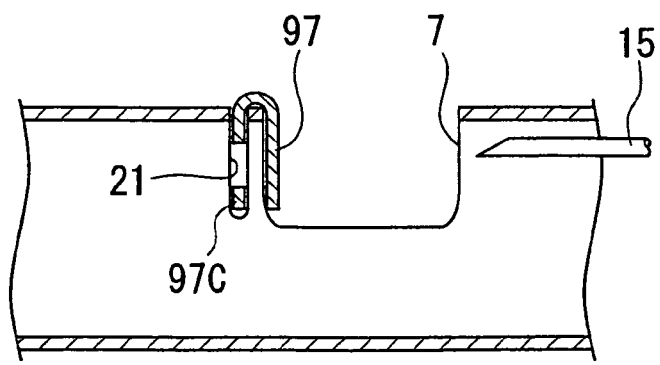

For example, in the first embodiment, the rectilinear portion 17B of the pledget 17 is supported by being inserted in the slit 21, however, as shown in FIG. 24, it is also possible to provide a convex portion 97C that protrudes outwards in a radial direction from a circular arc portion 97A of a pledget 97, and to provide support by inserting the convex portion 97C in the slit 21. In this case, as shown in FIGS. 25A and 25B, by placing the pledget 97 inside the side aperture 7, the same operation and effects as in the above described embodiments can be obtained.

Figure 26A:
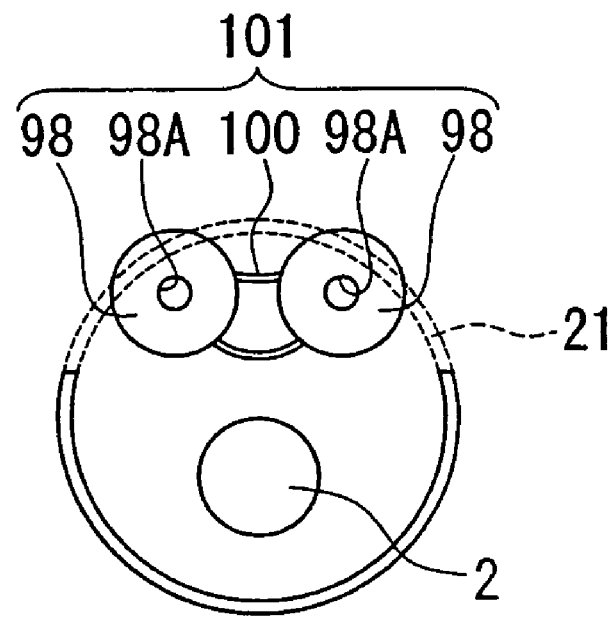
FIG. 26A is a front view and FIG. 26B is a view of a state after treatment showing the pledget of the ligature and suture device for medical application according to another embodiment of the present invention.
Figure 26B:
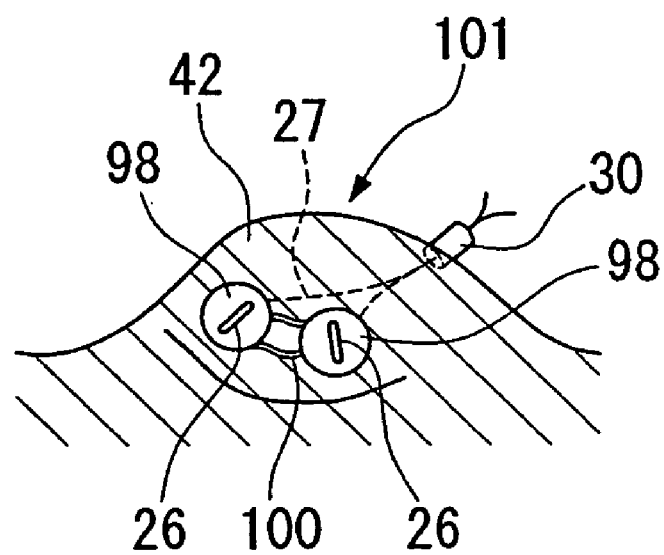

Furthermore, as shown in FIG. 26A, a pledget 101 that is provided with two small circular portions 98, in a center portion of which are provided holes 98A through which needles can be inserted, and a connecting thread 100 that connects the two small circular portions 98 can be used. In this case, it is possible to reduce the overall surface area of the pledget compared with the pledgets in each of the other embodiments described above, so that a reduction in space can be achieved, and interference with the endoscope can be decreased. Moreover, a portion of each of the small circular portions 98 can be fit into the slit 21 and, in the same way as in the above described embodiments, after the biomedical tissue 42 has been ligatured, the gap between the T-bars 26 can be prevented from becoming wider by the connecting thread 100. As a result, the same operation and effects as in the above described embodiments can be obtained.

Figure 27A:
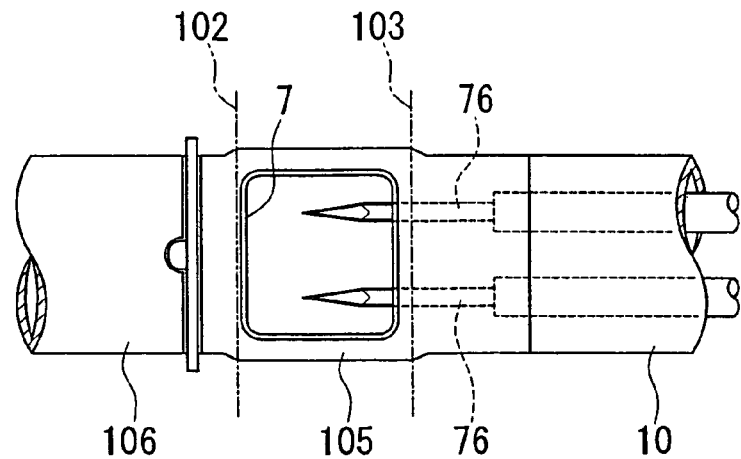
FIG. 27A is a frontal enlarged view and FIG. 27B is a side surface cross-sectional view showing principal portions of a ligature and suture system for medical application according to another embodiment of the present invention.
Figure 27B:
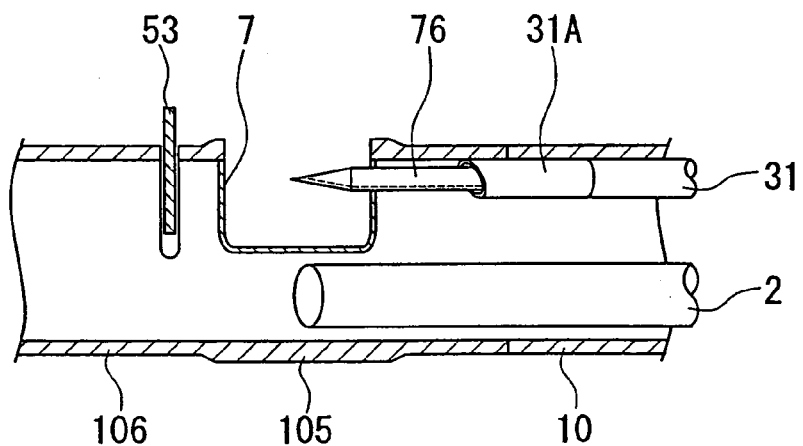

Furthermore, in the above described fifth embodiment, the reinforcing portion 75 is placed extending from the first position 11 to the second position 12, however, as shown in FIGS. 27A and 27B, it is also possible to take a first position 102 as the distal end of the side aperture 7, and a second position 103 as the base end of the side aperture 7, and to use a distal end portion 106 in which a reinforcing portion 105 is provided between the first position 102 and the second position 103. In addition, the reinforcing portion does not need to be provided by a thicker portion, and may be provided by a metal pipe or the like.

In this case, it is possible to suppress localized bending in the vicinity of the side aperture 7, in particular, and it is possible to favorably suppress shifting in the placement position of the pledget 17. The base end of the needles can also be reinforced so that wavering of the needles can be further suppressed.

Figure 28:
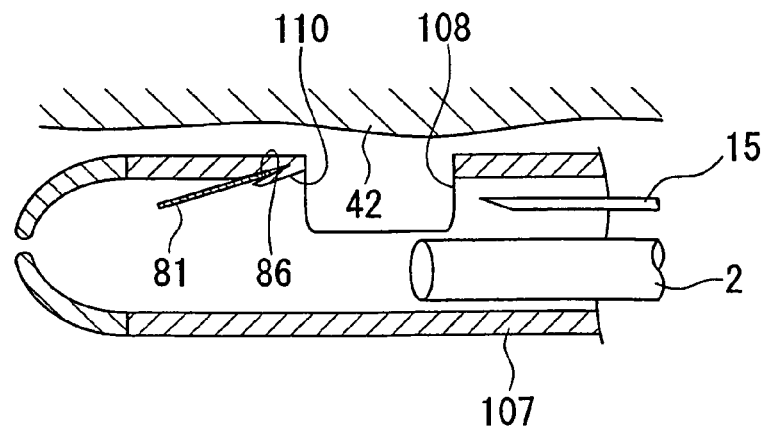
FIG. 28 is an enlarged view showing principal portions of a ligature and suture system for medical application according to another embodiment of the present invention.

Furthermore, in the above described sixth embodiment, a structure is employed in which the slit 86 in the pledget support portion 83 is formed extending from the distal end of the side aperture 85 further towards the distal end of the distal end portion 82, however, as shown in FIG. 28, it is also possible for the slit 86 to be formed in a slit support portion 110 so as to extend from the inner circumferential surface on the distal end side of a distal end portion 107 towards a side aperture 108.

In this case, the pledget 81 is placed at the distal end side in parallel with the internal wall of the distal end portion 107, and the pledget support portion 110 is deformed by the suction force generated when the biomedical tissue 42 is suctioned by the suction pump 5 of the endoscope 2, so that the orientation of the pledget 81 can be changed so as to be on the movement path of the needles 15.

Next, the eighth embodiment will be described with reference to FIGS. 29 through 35.

Note that the same symbols are allocated to the same component elements as those in the above described embodiments, and a description thereof is omitted.

Figure 29:
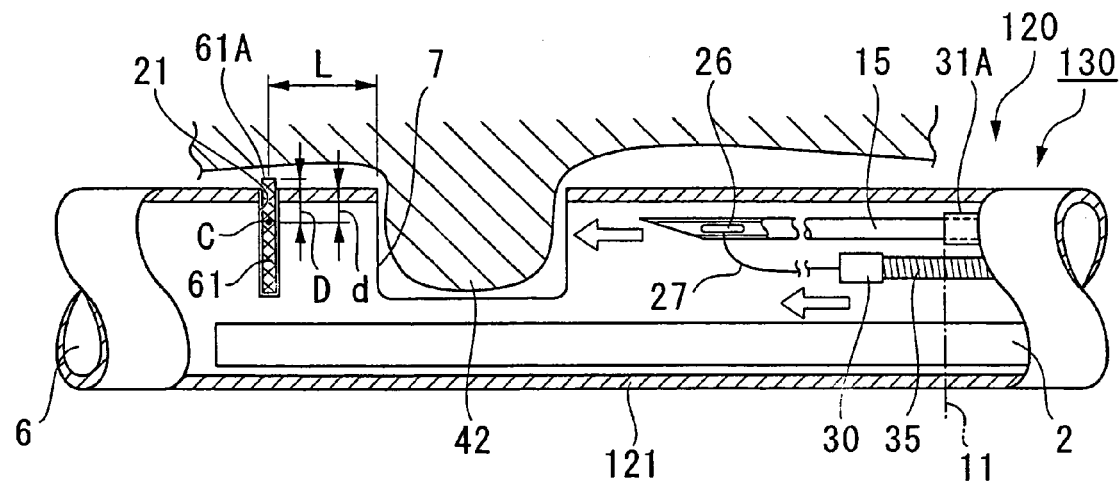
FIG. 29 is an enlarged view of principal portions showing a ligature and suture system for medical application according to an eighth embodiment of the present invention.

The eighth embodiment differs from the fourth embodiment in that, while the ligature and suture device for medical application 60 of the fourth embodiment is provided with the distal end needle guide portions 62, as shown in FIG. 29, the slit 21 of the ligature and suture device for medical application 120 of the present embodiment is placed at a distal end portion 121 at a predetermined spacing L from the distal end of the side aperture 7 so that, when moving the pledget 61, at least a portion of the pledget 61 is able to be removed before it arrives at the distal end of the side aperture 7.

The predetermined spacing L is determined using a formula:

$$L \geq (D^2 - d^2)^{1/2}$$

wherein a point punctured by the needle 15 when the pledget 61 is anchored in the slit 21 is taken as the needle puncture point C, the shortest distance from an arc portion (i.e., the edge portion) 61A of the pledget 61 to the needle puncture point C is taken as D, and the shortest distance from the slit 21 to the needle puncture point D is taken as d.

Figure 30:
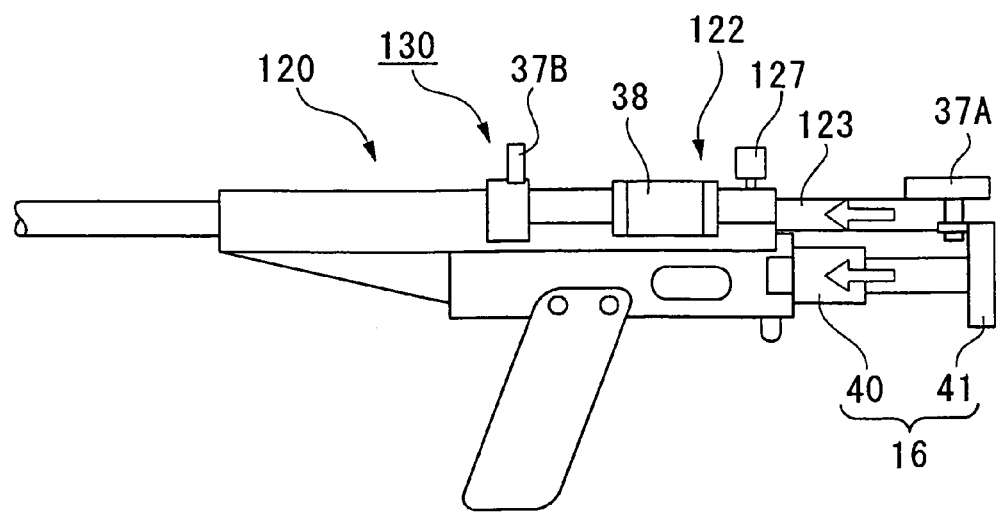
FIG. 30 is a schematic view showing a portion of the ligature and suture system for medical application according to the eighth embodiment of the present invention.
Figure 31:
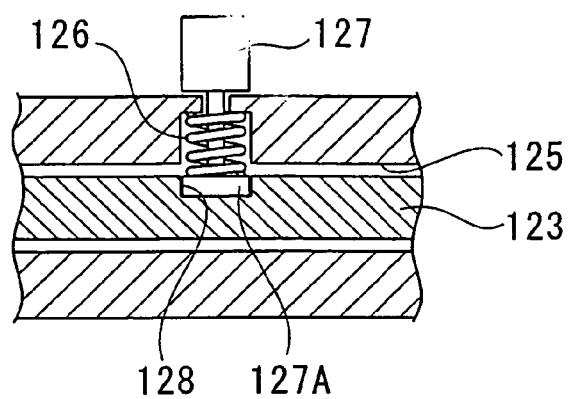
FIG. 31 is an enlarged cross-sectional view showing principal portions of the ligature and suture system for medical application according to the eighth embodiment of the present invention.

As shown in FIGS. 30 and 31, a ligature tool 122 is provided with a lock pin 127 that is urged by a spring 126 and is able to be pressed into and pulled out of an insertion hole 125 that houses a ligature tool operating member 123 such that the ligature tool operating member 123 is able to be moved freely backwards and forwards. A convex portion 127A is placed at a distal end of the lock pin 127, and a concave portion 128 that is able to be engaged with the convex portion 127A of the lock pin 127 is placed on a surface of the ligature tool operating member 123.

The concave portion 128 is placed at a position where it engages with the lock pin 127 in a state in which the distal end of the stopper 30 that is placed in a distal end of the ligature sheath 35 has been placed at the base end of the side aperture 7 by moving the ligature tool operating member 123 backwards or forwards.

Next, a description of a method of operating the ligature and suture device for medical application 120 and the ligature and suture system for medical application 130 according to the present embodiment, as well as the actions and effects thereof will be given.

Firstly, the suction process (S01) is performed in the same way as in the above described other embodiments and, as shown in FIG. 29, the biomedical tissue 42 is drawn inside the side aperture 7.

The routine then moves to an insertion process (S02).

As shown in FIG. 30, the pusher handle 41 is pushed in towards the distal end side so that the needles 15 are pushed out to the distal end side. In addition, the ligature tool operating member 123 is moved to the distal end side together with the pusher handle 41, and the ligature sheath 35 and the stopper 30 are moved together with the needles 15.

Figure 32:
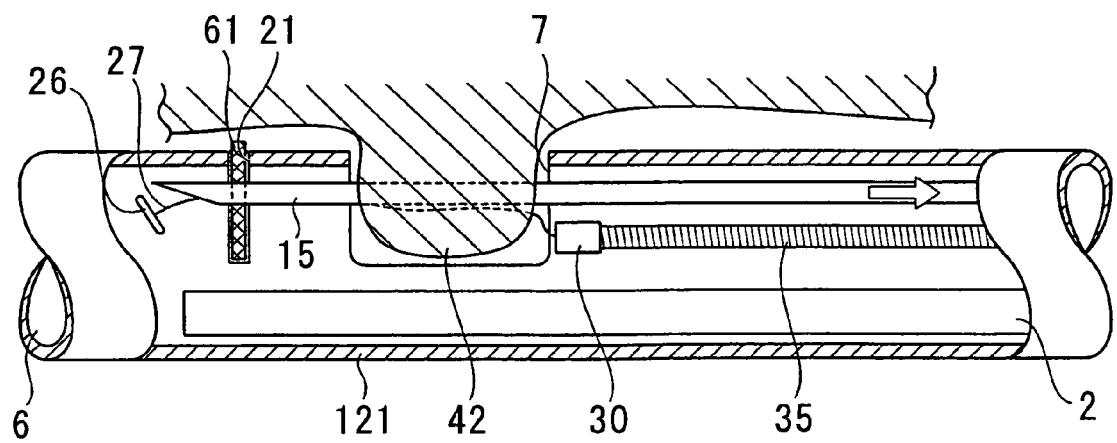
FIG. 32 is an explanatory view showing processing by the ligature and suture system for medical application according to the eighth embodiment of the present invention.

The routine then moves to a pushing out process (S03) and the pusher handle 41 is pushed out further. As a result, the pushing member (not shown) is moved to the distal end side relative to the needles 15, and, as shown in FIG. 32, the T-bars 26 inside the needles 15 are pushed to the distal side of the pledget 61.

After the T-bars 26 inside the needles 15 have been pushed to the distal end side of the pledget 61, as shown in FIG. 31, the lock pin 127 is engaged in the concave portion 128 of the ligature tool operating member 123 so that forward or backward movement of the ligature tool operating member 123 is stopped.

The routine then moves to the ligaturing process (S04).

Figure 33:
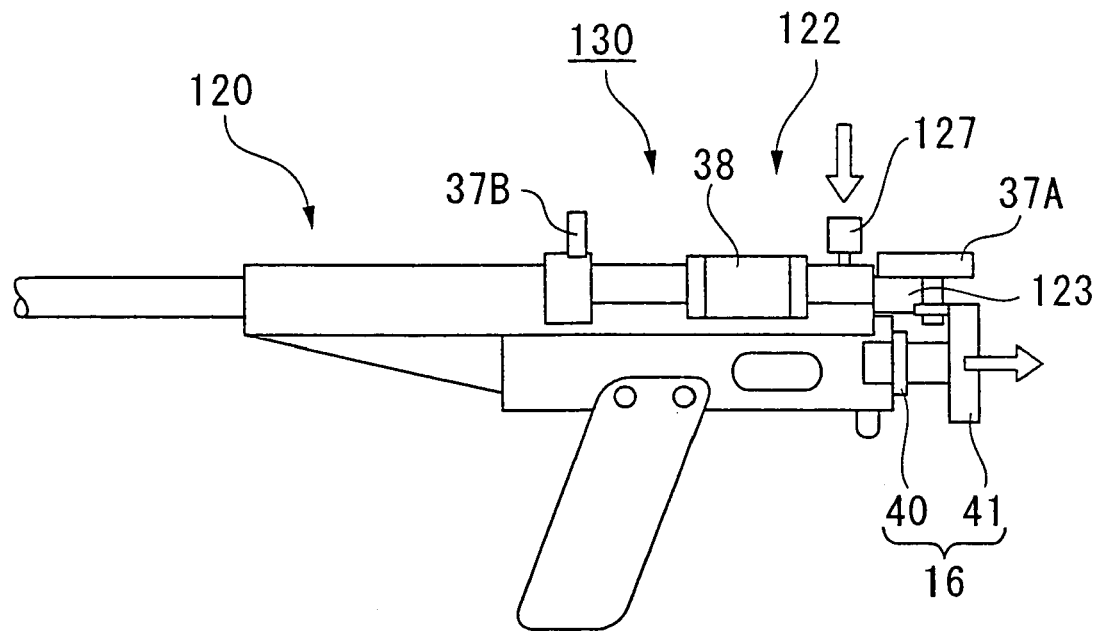
FIG. 33 is an explanatory view showing processing by the ligature and suture system for medical application according to the eighth embodiment of the present invention.

Namely, as shown in FIG. 33, if the pusher handle 41 is pulled to the base end side, the pushing member (not shown) is withdrawn inside the needles 15.

Figure 34:
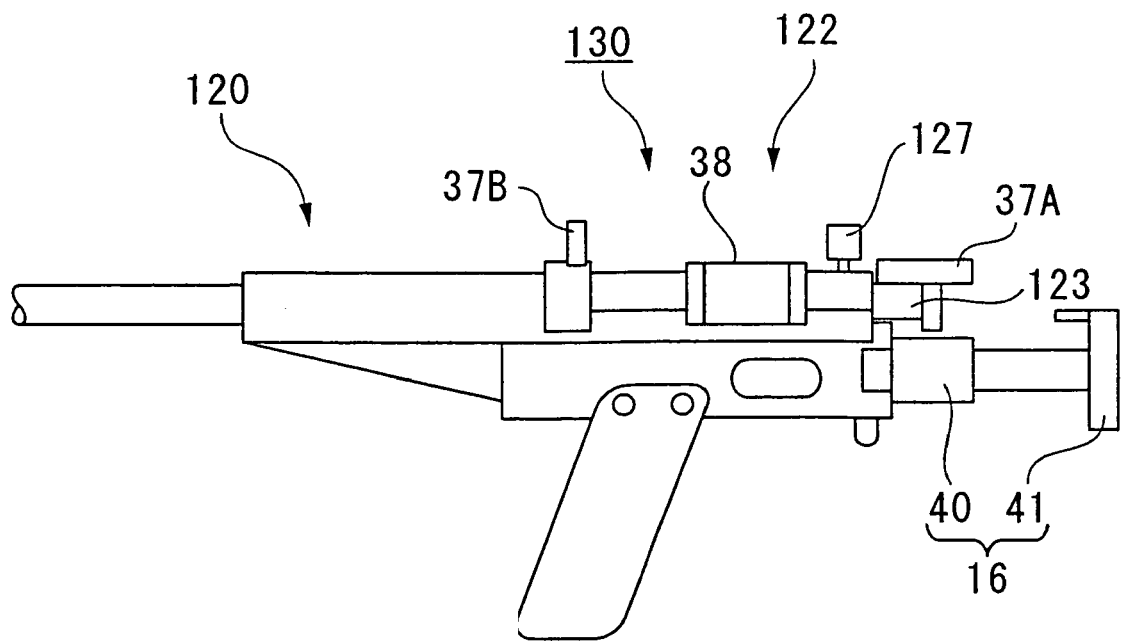
FIG. 34 is an explanatory view showing processing by the ligature and suture system for medical application according to the eighth embodiment of the present invention.

Furthermore, as shown in FIG. 34, if the pusher handle 41 is pulled in, then the needle handle 40 moves in conjunction with this, and the needles 15 are moved to the first position 11 shown in FIG. 29. At this time, the thread 27 is withdrawn from inside the needles 15, and the thread 27 is left in a state of being inserted inside the biomedical tissue 42.

Next, the ligature handle 38 is moved relative to the ligature tool operating member 123 from the second finger piece portion 37B in the direction of the first finger piece portion 37A. At this time, because the ligature sheath 35 does not move because it is engaged by the lock pin 127, the thread 27 is pulled into the ligature sheath 35 in a state in which the position of the ligature sheath 35 relative to the distal end portion 121 of the stopper 30 does not change.

Figure 35:
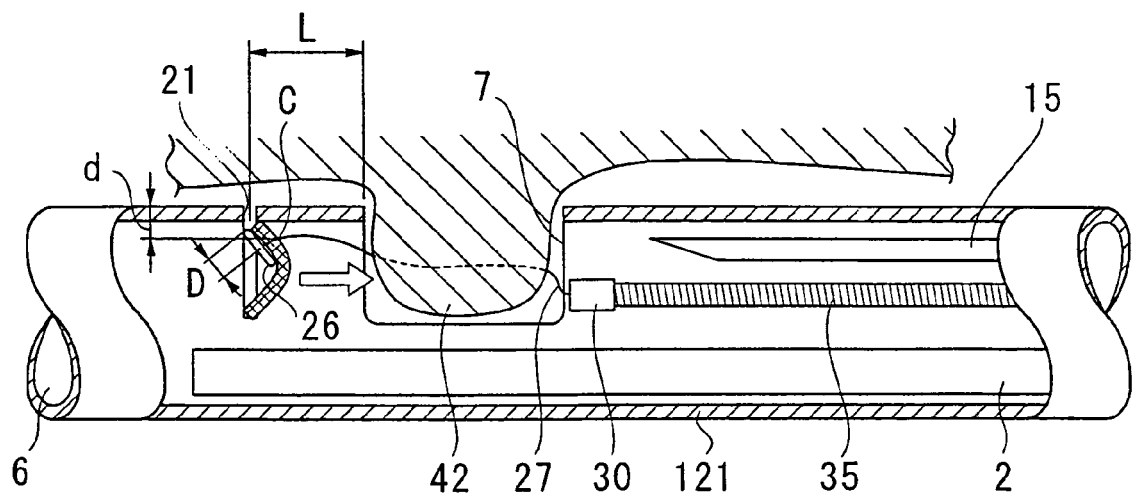
FIG. 35 is an explanatory view showing processing by the ligature and suture system for medical application according to the eighth embodiment of the present invention.

At this time, as shown in FIG. 35, the pledget 61 is pulled towards the operator side while being deformed with the needle puncture point C being in the foremost position.

Here, when the shortest distance from the arc portion 61A of the pledget 61 to the needle puncture point C is taken as D, and when the shortest distance from the slit 21 to the needle puncture point C is taken as "d", then the slit 21 and the side aperture 7 are separated by a distance determined by $L \geq (D^2 - d^2)^{1/2}$. Therefore, a space is formed between the side aperture 7 and the slit 21. Accordingly, as in the first embodiment shown in FIG. 9 (b), even without first moving the distal end portion 121 in the distal end direction, the pledget 61 is removed from the slit 21 before it is pushed by the biomedical tissue 42, and the biomedical tissue 42 is fastened in this state with the T-bars 26 in a state of press-contact with the pledget 61.

Forceps 43 that have been inserted in a channel in the endoscope 2 are made to protrude from the distal end of the endoscope 2 and cut the thread 27.

In this manner, the distal end portion 121 is moved away from the biomedical tissue 42, and the biomedical tissue 42 is removed from the side aperture 7, and the biomedical tissue 42 is ligatured in a bulging state together with the pledget 61.

According to this ligature and suture device for medical applications 120 and the ligature and suture system for medical applications 130, because the slit 21 is placed at a distance $L \geq (D^2 - d^2)^{1/2}$ away from the distal end of the side aperture 7, when moving the pledget 61 it is possible to remove at least a portion of the pledget 61 from the slit 21 before the pledget 61 arrives at the distal end of the side aperture 7.

Accordingly, without having to first move the distal end portion 121 forwards, it is possible to remove the biomedical tissue 42 from the side aperture 7 and it is possible to remove the pledget 61 easily and also lessen the work of an operation.

Next, the ninth embodiment will be described with reference to FIGS. 36 through 38B.

Note that the same symbols are allocated to the same component elements as those in the above described embodiments, and a description thereof is omitted.

Figure 36:
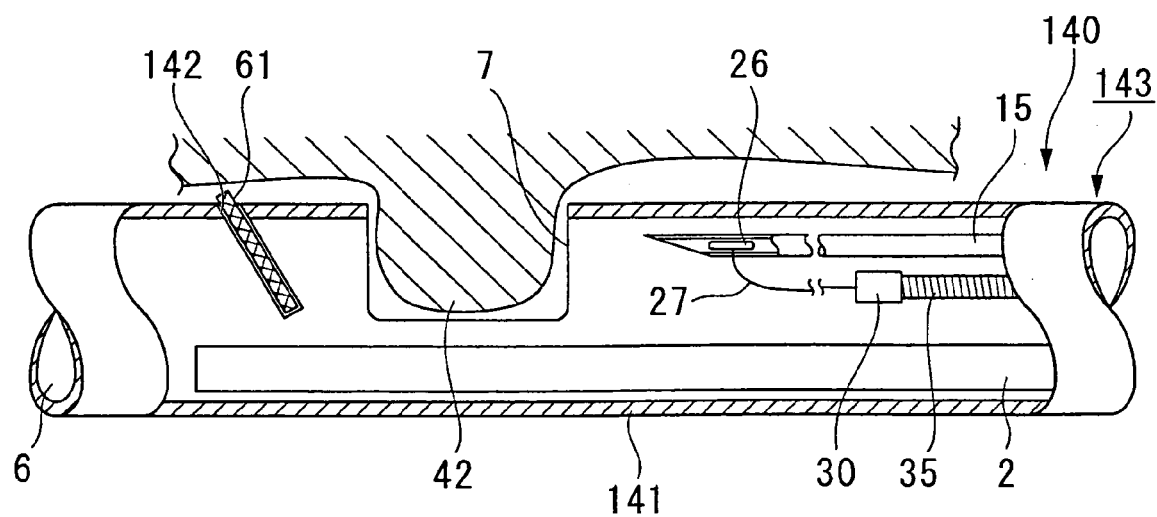
FIG. 36 is an enlarged view of principal portions showing a ligature and suture system for medical application according to a ninth embodiment of the present invention.

The ninth embodiment differs from the eighth embodiment in that, as shown in FIG. 36, a slit 142 that is placed at a distal end portion 141 of the ligature and suture device for medical applications 140 of the present embodiment intersects the lumen 6 at an oblique direction, and in that the distal end side is placed so as to extend on a slant towards the side aperture 7 side.

Figure 37:
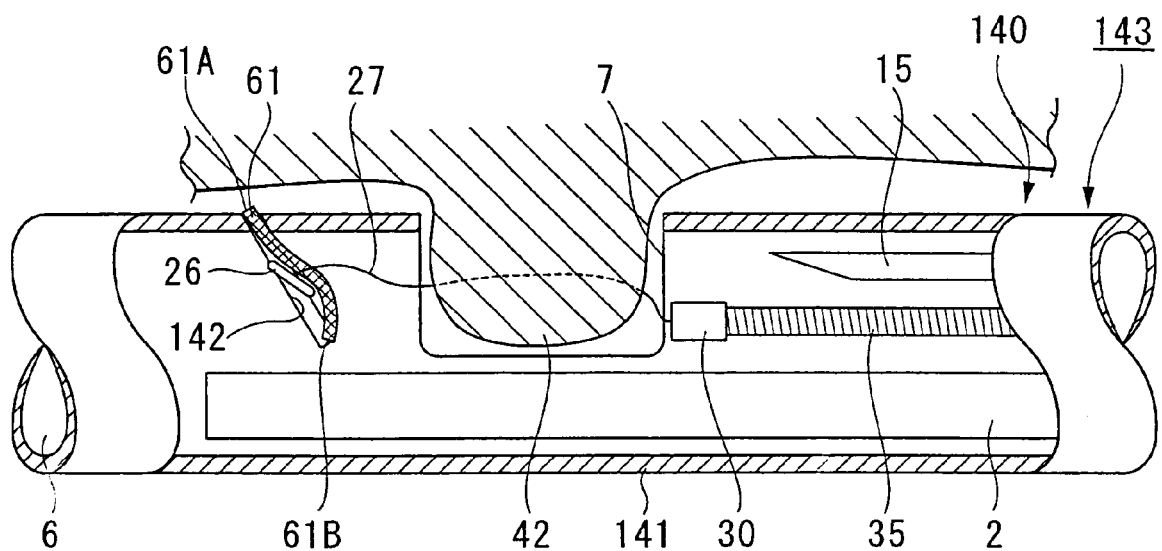
FIG. 37 is an explanatory view showing processing by the ligature and suture system for medical application according to the ninth embodiment of the present invention.
Figure 38A:
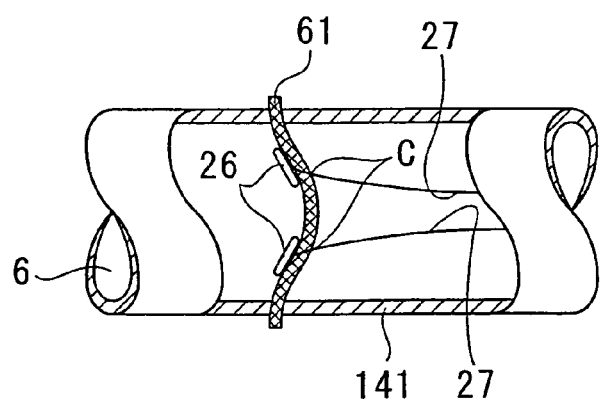
Figure 38B:
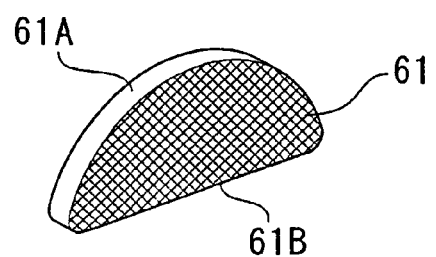
FIG. 38B is a perspective view showing a pledget of the ligature and suture system for medical application according to the ninth embodiment of the present invention.

When performing processing using this ligature and suture device for medical applications 140 and ligature and suture system for medical applications 143, in the same way as in the above described eighth embodiment, in the ligaturing process (S04), the ligature handle 38 is moved relative to the ligature tool operating member 123 from the second finger piece portion 37B in the direction of the first finger piece portion 37A so that the thread 27 is pulled into the ligature sheath 35. At this time, as shown in FIGS. 37 and 38A, because the direction of the slit 142 is close to the direction in which the pledget 61 is removed, when the pledget 61 is pulled towards the operator side while being deformed with the needle puncture point C being in the foremost position, the resistance to the slit 142 when the pledget 61 is being pulled out is reduced, and the pledget 61 is removed sequentially from the rectilinear portion 61B side of the pledget 61 that is sandwiched by the distal end portion side of the slit 142 that approaches the closest to the side aperture 7.

According to this ligature and suture device for medical applications 140 and this ligature and suture system for medical applications 143, the direction in which the slit 142 extends can be made close to the direction of movement of the pledget 61. In addition, resistance to the slit 142 when the pledget 61 is being pulled out is reduced, and the pledget 61 can be moved easily along the slit 142.

Figure 39:
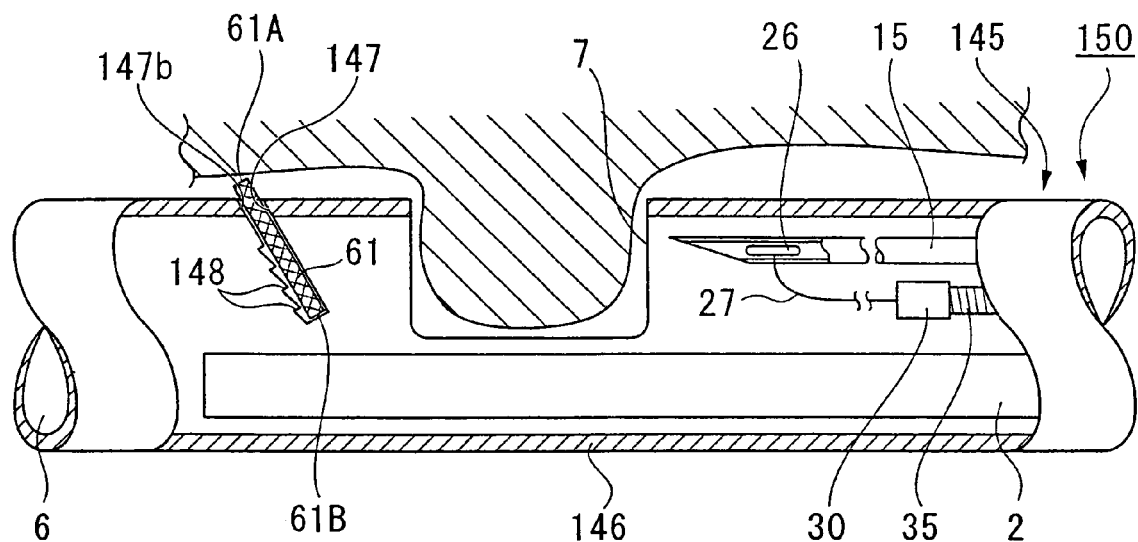
FIG. 39 is an enlarged view of principal portions showing a ligature and suture system for medical application according to a tenth embodiment of the present invention.
Figure 40:
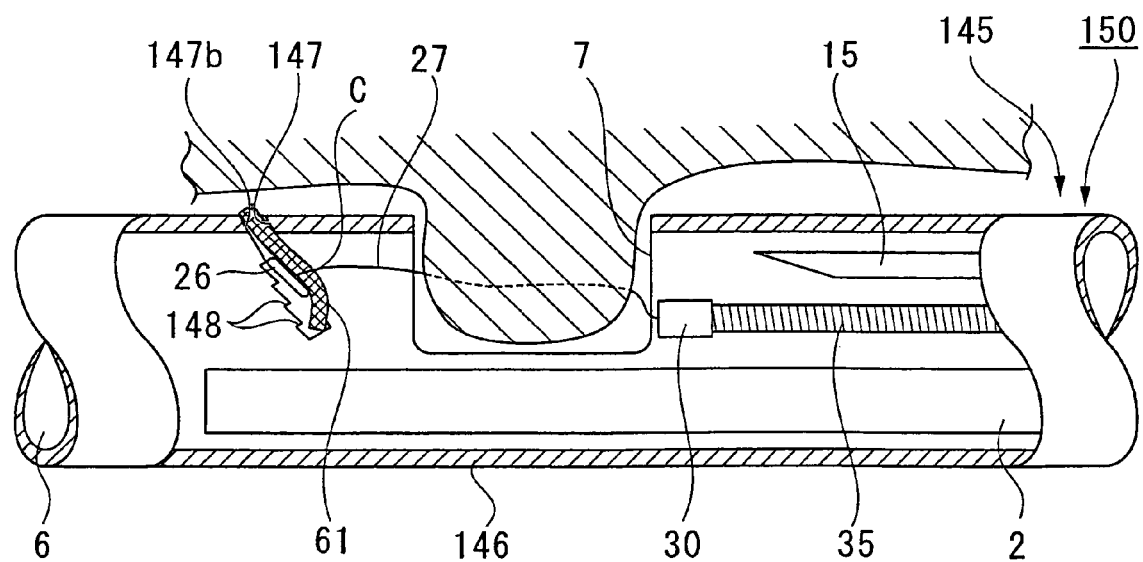
FIG. 40 is an explanatory view showing processing by the ligature and suture system for medical application according to the tenth embodiment of the present invention.

Next, the tenth embodiment will be described with reference to FIGS. 39 and 40.

Note that the same symbols are allocated to the same component elements as those in the above described embodiments, and a description thereof is omitted.

The tenth embodiment differs from the ninth embodiment in that jaw portions 148 that protrude gradually towards the terminal end side of the slit 147 are placed on a side surface 147b on a distal end side relative to the side aperture 7 of the slit 147 that is placed at a distal end portion 146 of the ligature and suture device for medical applications 145 of the present embodiment.

Here, because the arc portion 61A of the pledget 61 has a larger diameter than that of the distal end portion 146, the arc portion 61A of the pledget 61 protrudes from the outer surface of the distal end portion 146 and is press inserted into the slit 147. Accordingly, when the distal end portion 146 is inserted from the aperture, the pledget 61 is placed in contact with the internal wall of the esophagus and, due to the friction force that is consequently generated the pledget 61 receives force that is exerted outwards in the radial direction.

However, according to this ligature and suture device for medical applications 145 and this ligature and suture system for medical applications 150, because the jaw portions 148 are placed protruding gradually towards the terminal end side of the slit 147, the jaw portions 148 are able to press the pledget 61 so as to restrict the movement of the pledget 61 and reliably hold the pledget 61.

On the other hand, when pulling out the pledget 61 after puncturing has been achieved using the needles 15, because the jaw portions 148 protrude gradually in the direction in which the pledget 61 is removed, the jaw portions 148 offer no resistance to the movement of the pledget 61 and it is possible to easily withdraw the pledget 61 from the terminal end side of the slit 147 into the interior of the lumen 6.

Note that it is also possible for the jaw portions 148 to be placed on the side surface on the near side to the aperture 7.

Next, the eleventh embodiment will be described with reference to FIGS. 41 through 44.

Note that the same symbols are allocated to the same component elements as those in the above described embodiments, and a description thereof is omitted.

The eleventh embodiment differs from the tenth embodiment in that a variable member 158 that is able to be placed in contact with the pledget 61 and that alters at least a portion of the width of a slit 157 is placed at a side surface 15 on the side aperture 7 side of the slit 157 that has been placed at the distal end portion 156 of the ligature and suture device for medical applications 155 of the present embodiment.

Figure 41:
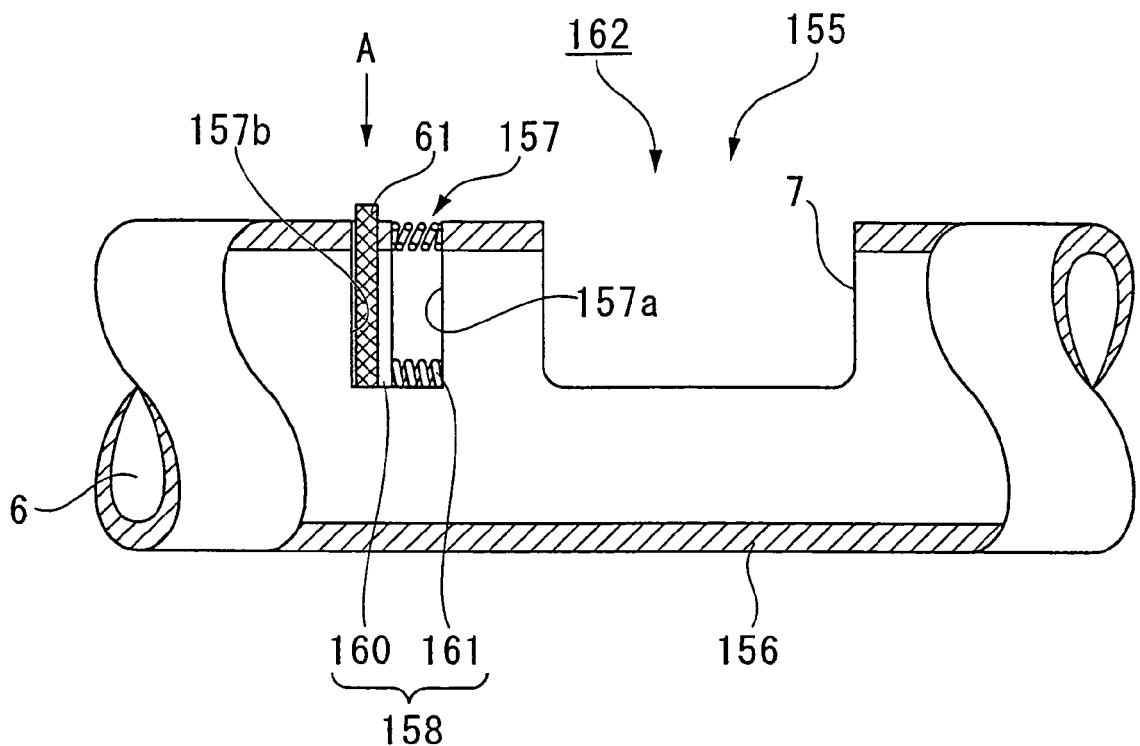
FIG. 41 is an enlarged view of principal portions showing a ligature and suture system for medical application according to an eleventh embodiment of the present invention.
Figure 42:
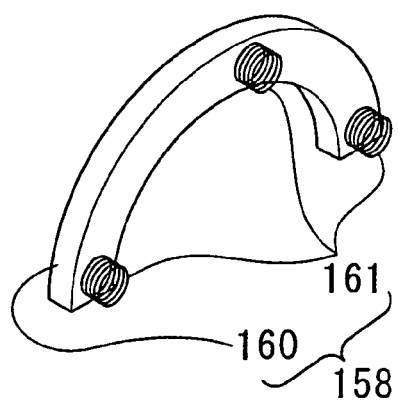
FIG. 42 is a perspective view showing a variable member of the ligature and suture system for medical application according to an eleventh embodiment of the present invention.

The slit 157 extends in the plate thickness direction of the distal end portion 156 as does the slit 21 in the above described other embodiments, and is formed having a larger width that the slit 21. As shown in FIGS. 41 and 42, the variable member 158 is provided with a pressing plate 160 that is formed in a semicircular shape that matches the arc portion 61A of the pledget 61, and springs (i.e., elastic members) 161 that protrude in the transverse direction of the slit 157 from the side surface 157a of the slit 157 on the near side of the side aperture 7 and urge the pressing plate 160 in, for example, three locations.

Next, a description of a method of operating the ligature and suture device for medical application 155 and the ligature and suture system for medical application 162 according to the present embodiment, as well as the actions and effects thereof will be given.

Figure 43:
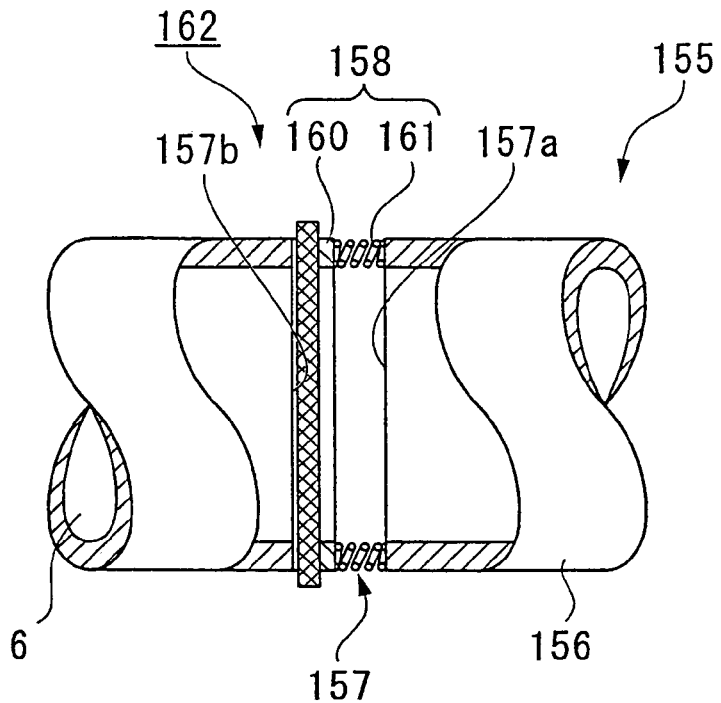
FIG. 43 is an enlarged view of principal portions showing a ligature and suture system for medical application according to an eleventh embodiment of the present invention.

Firstly, as shown in FIG. 43, the pledget 61 is press-inserted between the side surface 157b on the far side relative to the side aperture 7 of the slit 157 and the pressing plate 160 of the variable member 158. After the distal end portion 156 has been inserted into a body cavity, the suction process (S01) is performed in the same way as in the above described other embodiments and, as shown in FIG. 29, the biomedical tissue 42 is drawn inside the side aperture 7.

The routine then moves to the insertion process (S02).

The pusher handle 41 is pushed in towards the distal end side so that the needles 15 are pushed out on the distal end side. In addition, the ligature tool operating member 123 is moved to the distal end side together with the pusher handle 41, and the ligature sheath 35 and the stopper 30 are moved together with the needles 15.

Here, when the biomedical tissue 42 and the pledget 61 are punctured by the needles 15, because the needles 15 push the pledget to the side surface 157b side of the slit 157, the variable member 159 is maintained in its current state and the width of the slit 157 does not change.

Next, the routine moves to the pushing out process (S03) and the T-bars 26 are pushed to the far side of the pledget 61. The routine then moves to the ligaturing process (S04).

Figure 44:
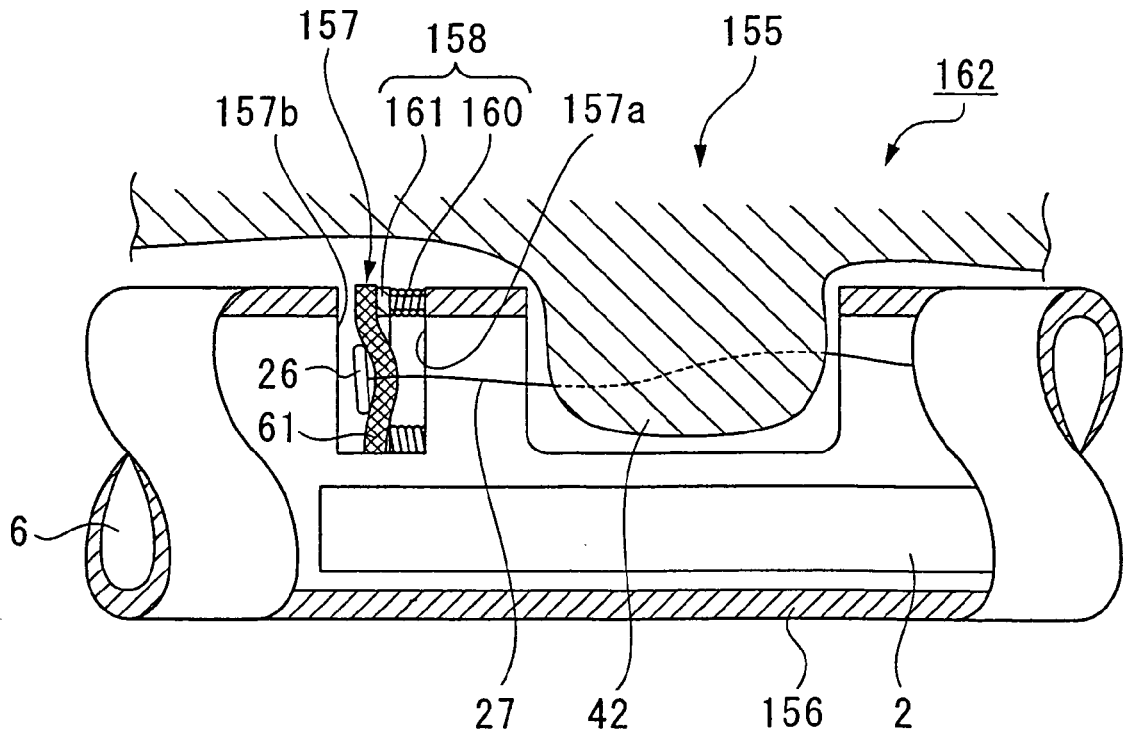
FIG. 44 is an explanatory view showing processing by the ligature and suture system for medical application according to the eleventh embodiment of the present invention.

When the thread 27 that has been inserted into the pledget 61 is pulled into the ligature sheath 35, it is pulled by the T-bars 26 and the pledget 61 moves to the side surface 157a side. At this time, as shown in FIG. 44, the pledget 61 presses the pressing plate 160 so as to move it to the side surface 157a side while compressing the spring 161, thereby enlarging the width of the slit 157.

In this manner, the pledget 61 can be easily removed from the widened slit 157.

According to this ligature and suture device for medical applications 155 and this ligature and suture system for medical applications 162, it is possible to change the width of the slit such that the pledget 61 can be press-inserted therein to match the thickness of the pledget 61.

Moreover, when the T-bars 26 are moved to the side aperture 7 side after the pledget 61 has been punctured by the needles 15, the pledget 61 presses against the pressing plate 160 so as to compress and deform the spring 161 and enable the width of the slit 157 to be widened. This enables the pledget 61 to be easily pulled out.

Figure 45:
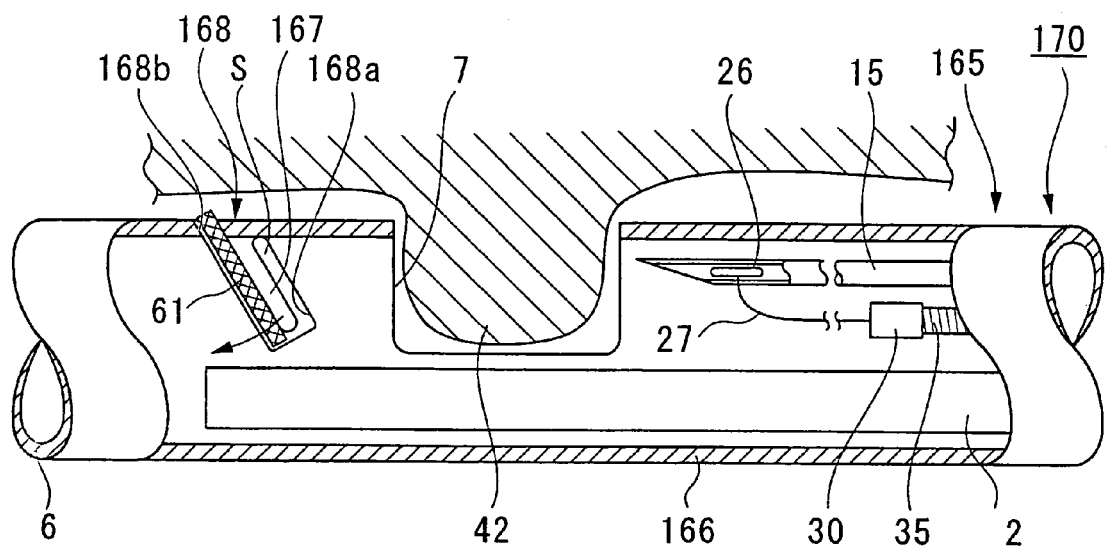
FIG. 45 is an enlarged view of principal portions showing a ligature and suture system for medical application according to a twelfth embodiment of the present invention.
Figure 46:
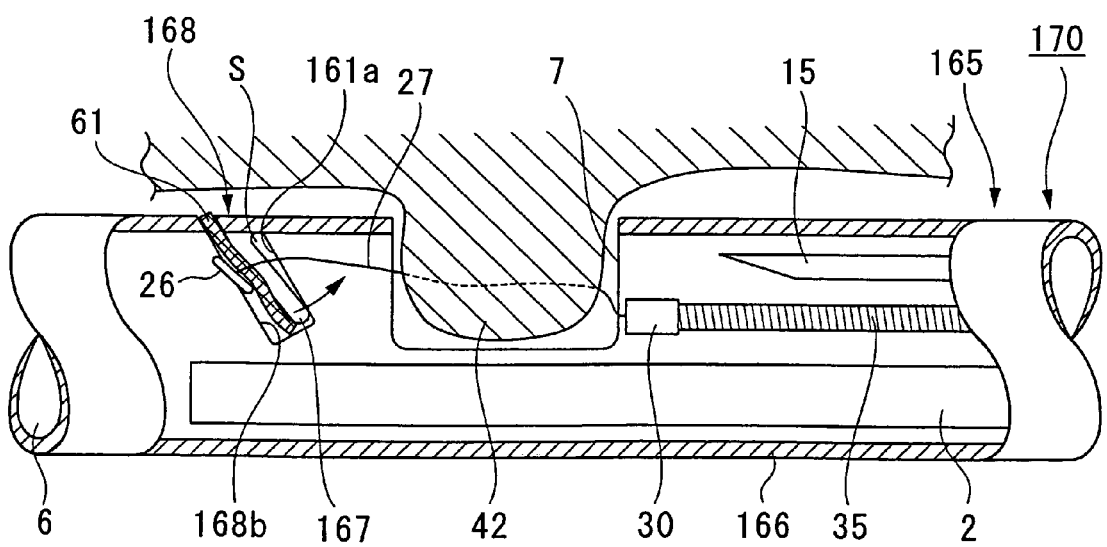
FIG. 46 is an explanatory view showing processing by the ligature and suture system for medical application according to the twelfth embodiment of the present invention.
Figure 47:
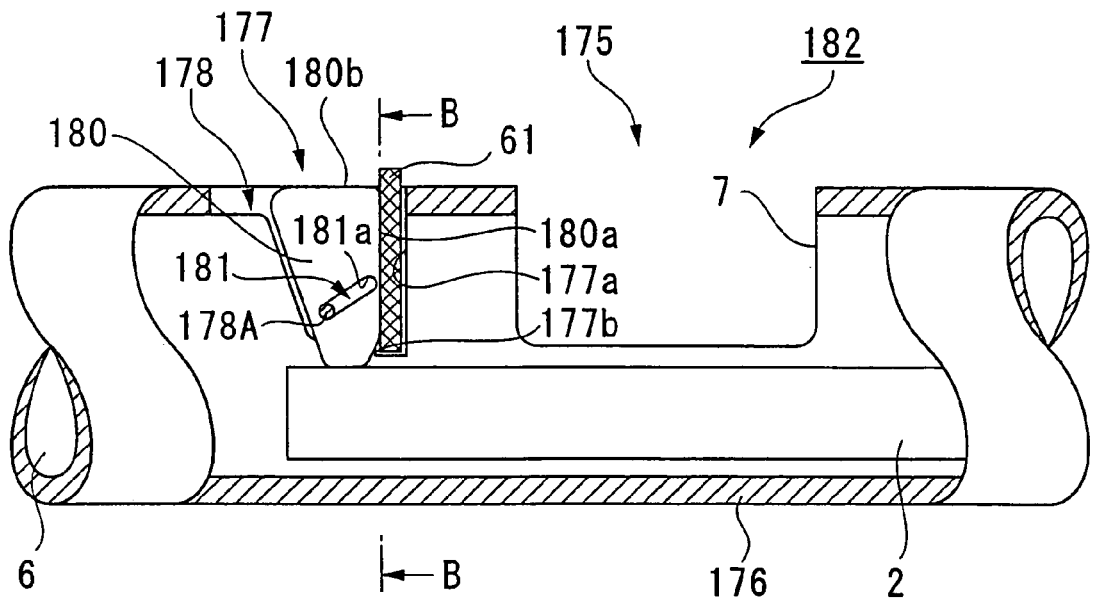
FIG. 47 is an enlarged view of principal portions showing a ligature and suture system for medical application according to a thirteenth embodiment of the present invention.
Figure 48:
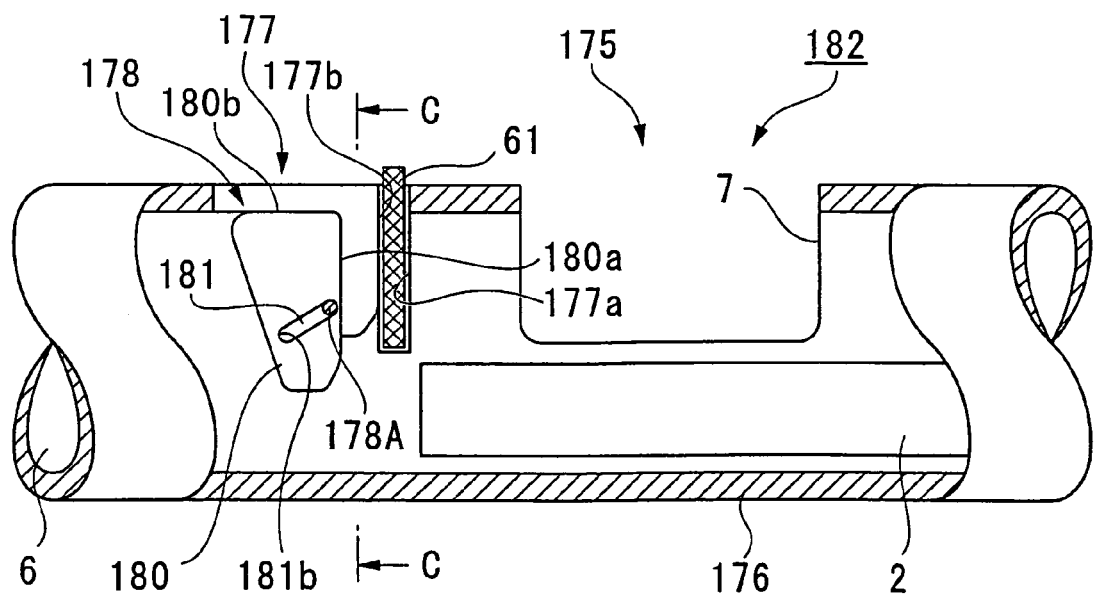
FIG. 48 is an enlarged view of principal portions showing a ligature and suture system for medical application according to a thirteenth embodiment of the present invention.
Figure 49A:
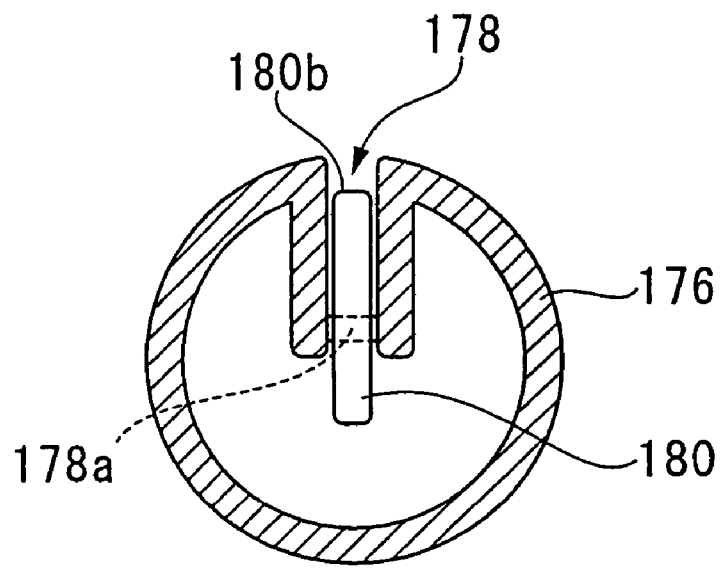
Figure 49B:
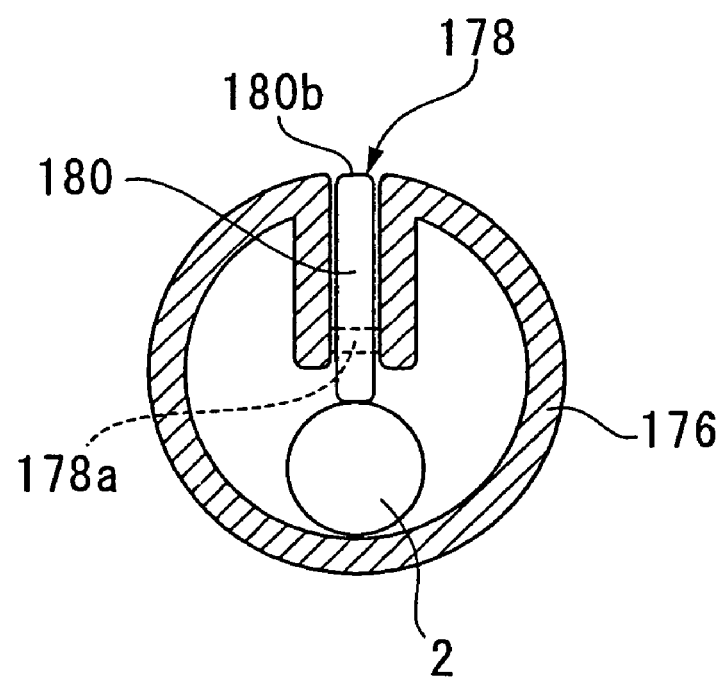
FIG. 49B is a cross-sectional view taken along a line C-C in FIG. 48.

Next, the twelfth embodiment will be described with reference to FIG. 45 and FIG. 46.

Note that the same symbols are allocated to the same component elements as those in the above described embodiments, and a description thereof is omitted.

The twelfth embodiment differs from the eleventh embodiment in that a variable member 167 that is placed at a distal end portion 166 of the ligature and suture device for medical applications 165 of the present embodiment is formed by a portion of a wall surface of the distal end portion 166, and is able to be elastically deformed.

In the same way as the slits 142 and 147, the slit 168 is formed extending in an oblique direction relative to the lumen 6, and protrudes from a central portion of a side surface 168a of the slit 168 on the nearer side relative to the side aperture 7 towards the side surface 168b side of the slit 168. In addition, a substantially constant gap S is provided away from the side surface 168a and extending towards the terminal end side. The variable member 167 is formed having a plate thickness that enables the pledget 61 to be press-inserted between the variable member 167 and the side surface 168b of the slit 168 on the far side relative to the side aperture 7, while bending the variable member 167 towards the side surface 168a side of the slit 168.

Next, a description of a method of operating the ligature and suture device for medical application 165 and the ligature and suture system for medical application 170 according to the present embodiment, as well as the actions and effects thereof will be given.

Following the suction process (S01), the routine moves to the insertion process (S02) and the pusher handle 41 is pushed in towards the distal end side so that the needles 15 are pushed out on the distal end side. In addition, the ligature tool operating member 123 is moved to the distal end side together with the pusher handle 41, and the ligature sheath 35 and the stopper 30 are moved together with the needles 15.

Here, when the biomedical tissue 42 and the pledget 61 are punctured by the needles 15, because the needles 15 push the pledget to the side surface 168b side of the slit 168, the variable member 167 is maintained in its current state and the width of the slit 168 does not change.

Next, the routine moves to the pushing out process (S03) and the T-bars 26 are pushed to the far side of the pledget 61. The routine then moves to the ligaturing process (S04).

When the thread 27 that has been inserted into the pledget 61 is pulled into the ligature sheath 35, it is pulled by the T-bars 26 and the pledget 61 moves to the side aperture 7 side. At this time, the variable member 167 is pushed by the pledget 61 and is bent to the side surface 168a side, thereby enlarging the width of the slit 168.

In this manner, the pledget 61 can be easily removed from the widened slit 168.

According to this ligature and suture device for medical applications 165 and this ligature and suture system for medical applications 170, because the variable member 167 is formed as an elastically deformable portion of the distal end portion 166, the same operation and effects as those of the eleventh embodiment can be achieved without providing a separate component such as the spring 161. Accordingly, the number of components can be reduced.

Next, the thirteenth embodiment will be described with reference to FIG. 47 through FIG. 49B.

Note that the same symbols are allocated to the same component elements as those in the above described embodiments, and a description thereof is omitted.

The thirteenth embodiment differs from the twelfth embodiment in that a second slit 178 is formed extending further towards the far side along the lumen 6 from a center portion of a side surface 177b side, which is on the far side relative to the side aperture 7, of a slit 177 that is placed at a distal end portion 176 of the ligature and suture device for medical applications 175 of the present embodiment. In addition, the thirteenth embodiment differs in that a variable member 180 is formed in a plate shape and positioned so as be able to slide along the second slit 178.

In the variable member 180 are formed a first surface 180a that is substantially parallel with the side surface 177b of the slit 177, a second surface 180b that is orthogonal to the first surface 180a, and an elongated insertion hole 181 that extends in a direction that substantially cuts in two an angle formed by the first surface 180a and the second surface 180b.

In the second slit 178, a shaft portion 178A is inserted into the insertion hole 181 in the variable member 180 and is suspended in the width direction.

The length in the longitudinal direction of the first surface 180a of the variable member 180 is set to a length that, when the shaft portion 178A is positioned at one end 181a of the insertion hole 181, the shaft portion 178A protrudes in a radial direction of the lumen 6 to a position that is deeper than the side aperture 7 and is able to make contact with the endoscope 2 that has been inserted into the lumen 6, and when the shaft portion 178A is positioned at the other end 181b of the insertion hole 181, is set to a length that enable the shaft portion 178A to make contact with the surface of the endoscope 2 that has been inserted into the lumen 6.

Next, a description of a method of operating the ligature and suture device for medical application 175 and the ligature and suture system for medical application 182 according to the present embodiment, as well as the actions and effects thereof will be given.

Following the suction process (S01), when, in the insertion process (S02), there is a need to fix the pledget 61 stably to the distal end portion 176 such as when the pledget 61 is punctured by the needles 15, the endoscope 2 is inserted into the lumen 6. At this time, if the variable member 180 and the endoscope 2 are in contact, then the variable member 180 is restricted by the shaft portion 178A and is only able to move in the direction of the insertion hole 181. In addition, the distance between the first surface 180a of the variable member 180 and the side surface 177a of the slit 177 becomes less than the distance between the side surfaces 177a and 177b of the slit 177, so that the pledget 61 is also pushed between the first surface 180a of the variable member 180 and the side surface 177a of the slit 177.

When the pledget 61 is removed from the slit 177, the endoscope 2 is withdrawn from the lumen 6. At this time, the variable member 180 is moved by its own weight from the one end 181a to the other end 181b of the insertion hole 181, and the state of pressing between the first surface 180a of the variable member 180 and the side surface 177a of the slit 177 is released. Accordingly, the variable member 180 is separated from the pledget 61 and the pledget 61 can be easily removed from the slit 177.

Subsequent processing is the same as in the above described embodiments.

According to this ligature and suture device for medical applications 175 and ligature and suture system for medical applications 182, the pressing of the pledget 61 on the slit 177 can be released by moving the endoscope 2 backwards or forwards.

Next, the fourteenth embodiment will be described with reference to FIG. 50 through FIG. 52.

Note that the same symbols are allocated to the same component elements as those in the above described embodiments, and a description thereof is omitted.

Figure 50:
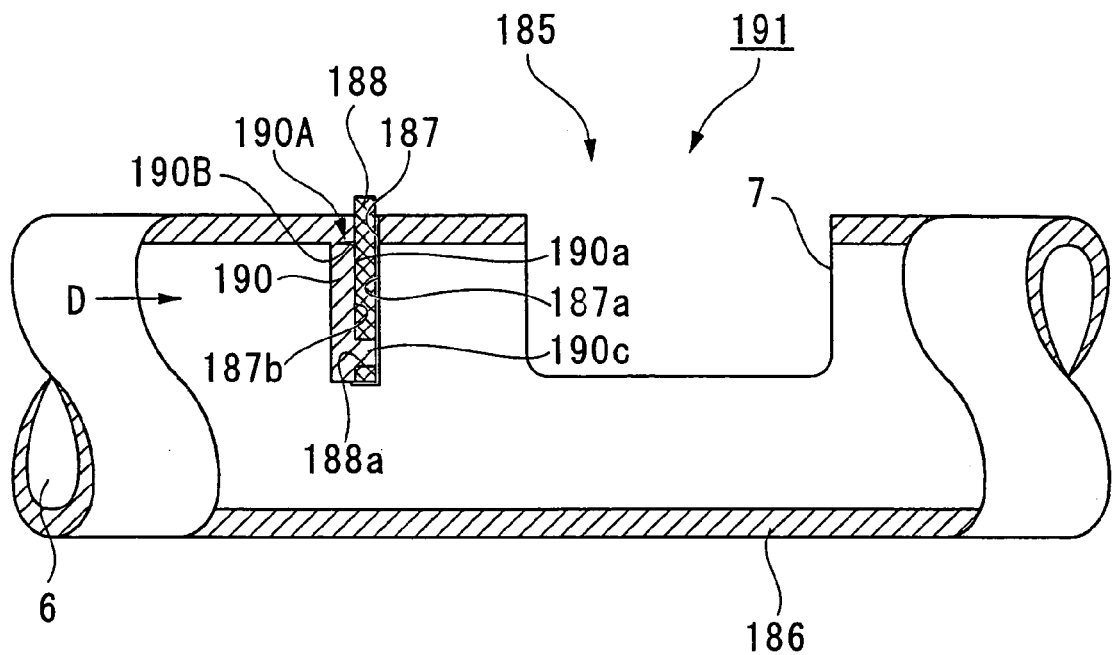
FIG. 50 is an enlarged view of principal portions showing a ligature and suture system for medical application according to a fourteenth embodiment of the present invention.

The fourteenth embodiment differs from the thirteenth embodiment in that, as shown in FIG. 50, a supporting plate 190 that supports a pledget 188 is provided in a slit 187 that is placed at a distal end portion 186 of the ligature and suture device for medical applications 185 of the present embodiment.

The slit 187 is formed extending in the plate thickness direction of the distal end portion 186 in the same way as the slit 157.

The supporting portion 190 is provided extending inwards in the radial direction of the distal end portion 186 along a side surface 187b that is on the far side relative to the side aperture 7 of the slit 187. A notch portion 190B that gradually opens wider as it approaches the far side of the side aperture 7 is provided at a base portion of the supporting portion 190. The notch portion 190B does not open up when the pledget 188 is press-inserted, but allows the supporting plate 190 to be bent at a wall surface of the distal end portion 186 when the supporting plate 190 is pressed by the needles 15.

In addition, a protruding bar portion 190C is provided on a surface 190a of the supporting plate 190 that faces the pledget 188 when the pledget 188 is press-inserted into the slit 187.

Figure 51:
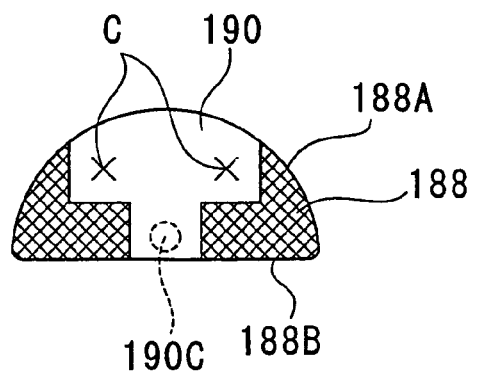
FIG. 51 is a view as seen from the direction indicated by an arrow D in FIG. 50.

As shown in FIG. 51, a hole portion 188a whose concave portion is able to fit together with the convex portion of the protruding bar portion 190C is provided in the pledget 188 in the vicinity of the center on the rectilinear portion 188B side of the needle puncture points C.

Next, a description of a method of operating the ligature and suture device for medical application 185 and the ligature and suture system for medical application 191 according to the present embodiment, as well as the actions and effects thereof will be given.

Following the suction process (S01), when, in the insertion process (S02), the needle puncture points C of the pledget 188 are punctured by the needles 15, the distal ends of the needles 15 come into contact with and press the supporting plate 190.

Figure 52:
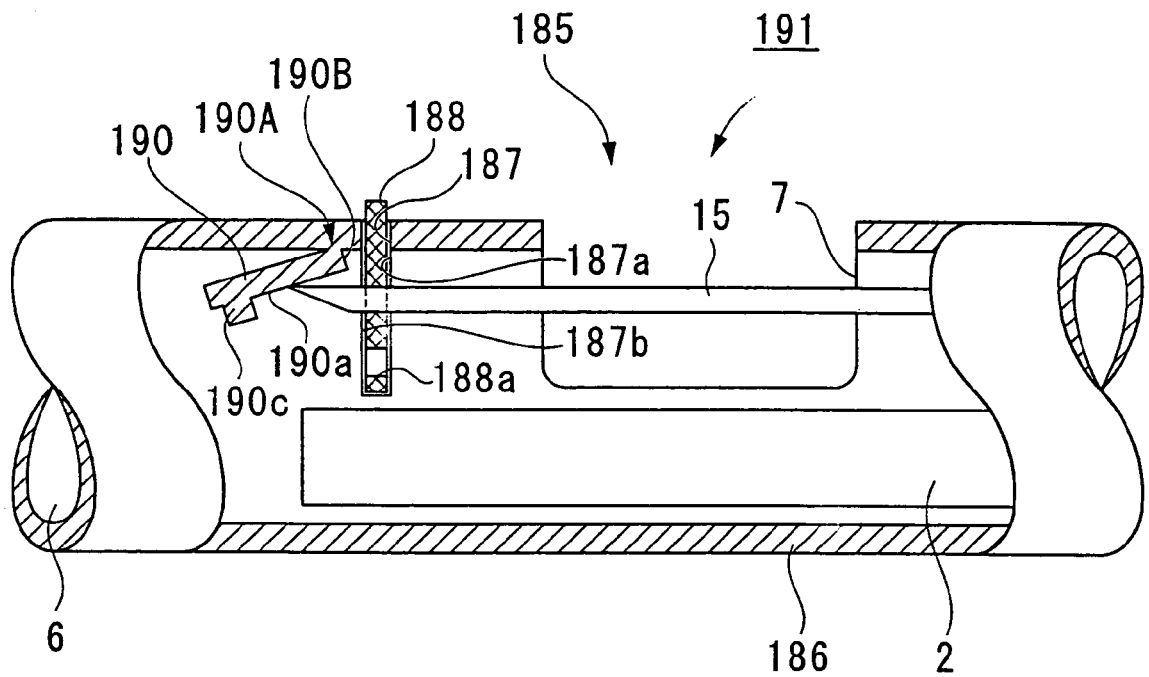
FIG. 52 is an explanatory view showing processing by the ligature and suture system for medical application according to the fourteenth embodiment of the present invention.
Figure 53:
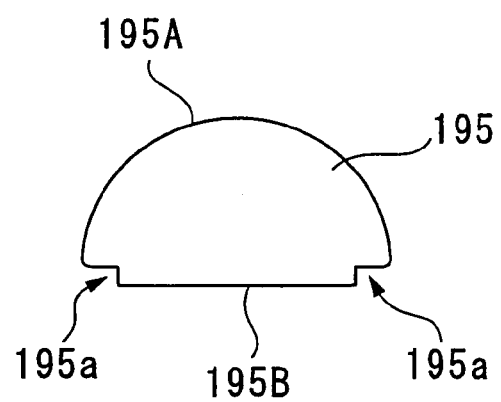
FIG. 53 is a frontal view showing a pledget of a ligature and suture device for medical application according to another embodiment of the present invention.
Figure 54:
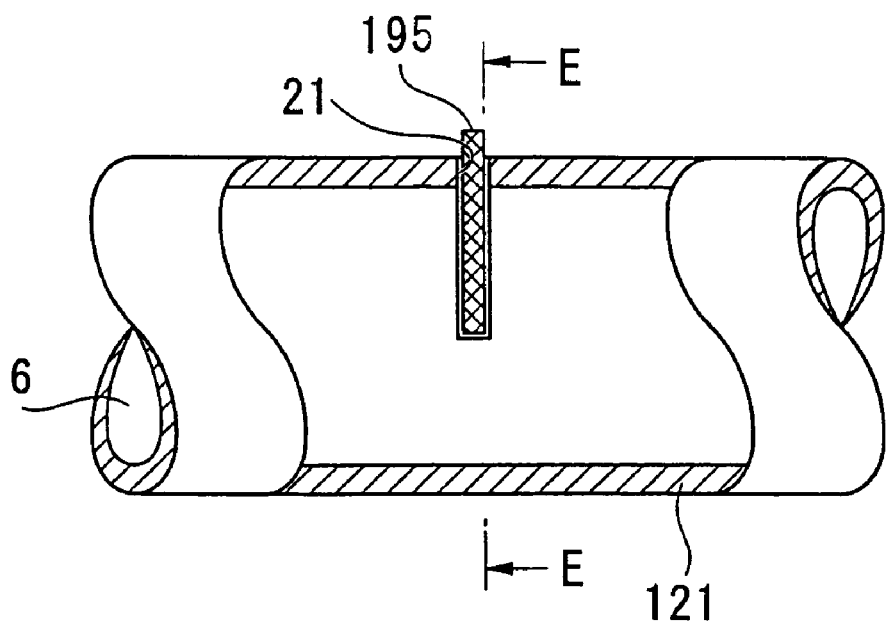
FIG. 54 is an enlarged view of principal portions showing a ligature and suture system for medical application according to another embodiment of the present invention.
Figure 55:
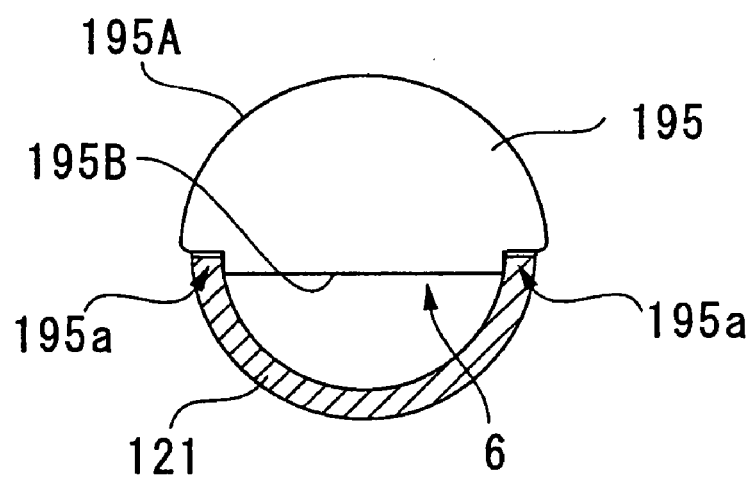
FIG. 55 is a cross-sectional view taken along a line E-E in FIG. 54.
Figure 56:
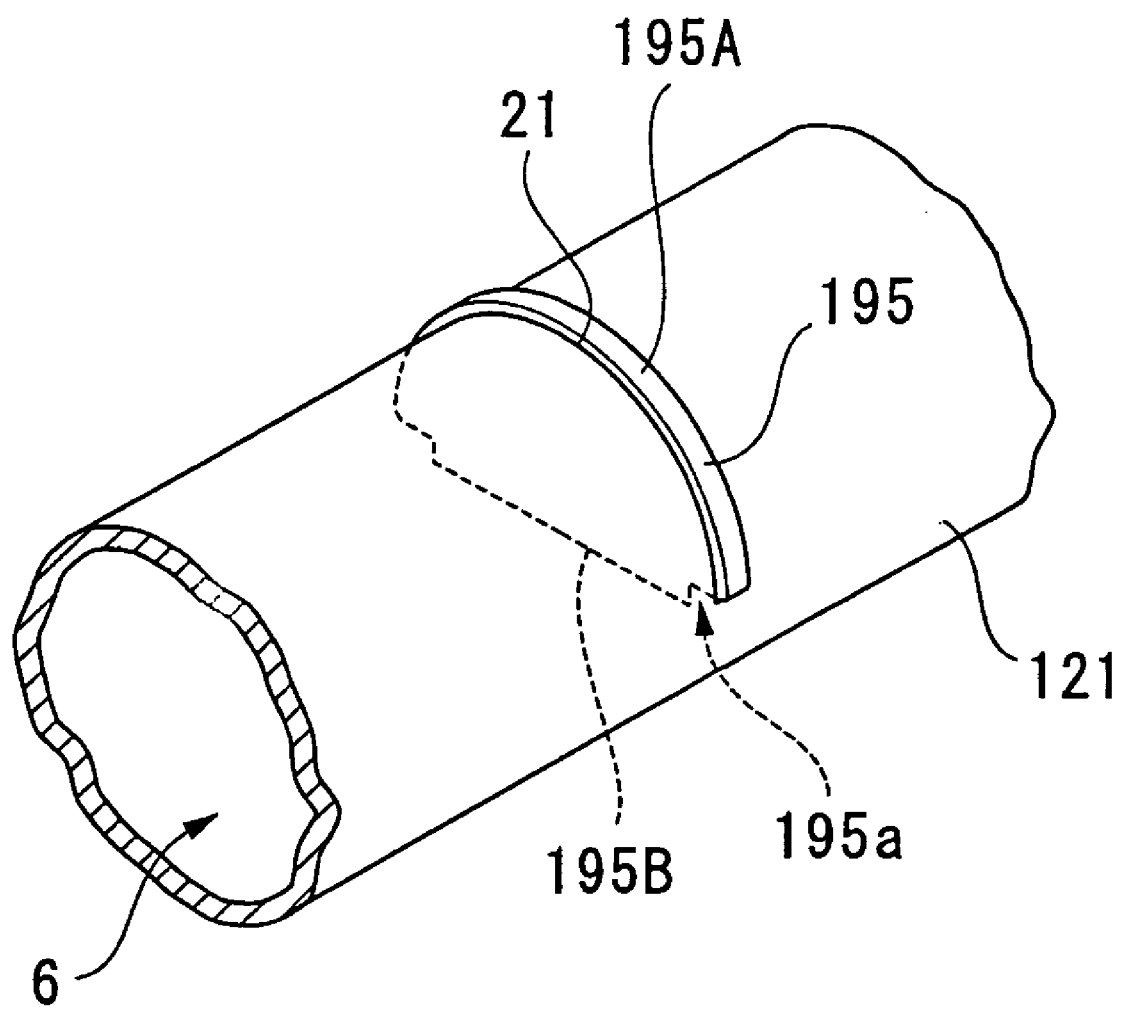
FIG. 56 is a perspective view of principal portions showing a ligature and suture system for medical application according to another embodiment of the present invention.

At this time, as shown in FIG. 52, the notch portion 190B of the supporting plate 190 opens up, and the state of engagement between the protruding bar portion 190C and the hole portion 188a of the pledget 188 is released. The supporting plate 190 is bent from the base portion 190A towards the distal end side of the lumen 6. As a result, the needles 15 once again move beyond the position of the slit 187 into the distal end portion 186.

Subsequent processing is the same as in the above described embodiments.

According to this ligature and suture device for medical applications 185 and ligature and suture system for medical applications 191, the removal of the pledget 61 can be achieved by moving the needles 15 backwards or forwards.

Here, as shown in FIGS. 53 through 56, it is also possible for incomplete portions 195a to be formed in the vicinity of the boundaries between an arc portion 195A and a rectilinear portion 195B of a pledget 195.

In this case, by making the incomplete portions 195a a size that enables them to be engaged, for example, with terminal end portions of the slit 21 of the distal end portion 121, the pledget 195 can be more stably press-inserted in the slit 21.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

The ligature and suture device of the invention for medical application enables biomedical tissue to be taken inside a side aperture in a distal end portion, and, when a needle is made to pierce the biomedical tissue that has been taken in and ligaturing or suturing is conducted using the suturing member, enables a pledget to be placed between the suturing member and the biomedical tissue, and suppresses any burying of the suturing member in the biomedical tissue.

The above ligature and suture device for medical application may further includes a protective member that protects a placement state of the pledget when the endoscope that has been inserted into the lumen is being operated.

According to the ligature and suture device of the invention, it is possible to suppress the pledget from moving or being deformed inside the distal end portion before and after the endoscope is operated, and the pledget can be more suitably pierced by a needle.

In the above ligature and suture device for medical application, the protective member may be placed in the distal end portion.

The ligature and suture device of the invention for medical application enables the pledget placement state to be maintained in a more suitable state in the vicinity of the pledget.

In the above ligature and suture device for medical application, the protective member may be a restricting member that restricts contact between the endoscope that has been inserted into the lumen and the pledget.

In the ligature and suture device of the invention for medical application, because contact between the endoscope and the pledget is restricted by the restricting member, it is possible to restrain the endoscope from coming into contact with the pledget and deforming the pledget, and to maintain the placement state of the pledget.

In the above ligature and suture device for medical application, the protective member may be placed on the pledget.

In the ligature and suture device of the invention for medical application, even if the endoscope and the pledget do come into contact, the placement state of the pledget can be maintained.

The above ligature and suture device for medical application may further include a distal end side needle guide portion that is placed further to the base end side of the distal end portion compared to the pledget, and that guides a distal end of the needle to the pledget.

The ligature and suture device of the invention for medical application enables the needle to be reliably guided to the pledget by causing the needle to be inserted along the distal end side needle guide portion.

In the above ligature and suture device for medical application, a reinforcing portion that increases a rigidity of the distal end portion may be provided in the distal end portion between at least the first position and the second position.

The ligature and suture device of the invention for medical application reduces wavering in the positional relationship between the needle and the side aperture and the pledget using the reinforcing member, and enables wavering of the needle at the moment of piercing by the needle to be suppressed, thereby enabling the needle to be reliably guided to the pledget and pierce the pledget.

In the above ligature and suture device for medical application, a reinforcing portion that increases a rigidity of the distal end portion may be provided in the distal end portion between at least the first position and the distal end side needle guide portion.

In the ligature and suture device for medical application, when the distal end side needle guide portion is provided, the needle can be reliably guided to the distal end side by the distal end side needle guide portion. Accordingly, the length of the reinforcing portion can be shortened, and the rigid portion of the distal end portion can be reduced to the minimum necessary.

In the above ligature and suture device for medical application, a slit into which the pledget can be press-inserted may be provided so as to open onto a side surface of the distal end portion between the side aperture and the second position.

In the ligature and suture device of the invention for medical application, by press-inserting the pledget in the slit, the pledget can be aligned in a perpendicular direction relative to the movement path of the needle, and penetration by the needle can be reliably performed. Moreover, the pledget can be easily removed by being pulled from the inner side in the radial direction.

In the above ligature and suture device for medical application, the insertion portion may be provided with a pledget anchoring portion that anchors the pledget such that the pledget can be freely removed and anchored again, and the pledget anchoring portion may be formed such that, when the pledget is being moved, at least a portion of the pledget can be removed before the pledget arrives at a distal end of the side aperture, and the pledget anchoring portion is placed a predetermined distance apart from a distal end of the side aperture.

In the ligature and suture device of the invention for medical application, because the pledget anchoring portion is placed a predetermined distance apart from a distal end of the side aperture, the pledget can be deformed by pulling the pledget using the suturing member when the suturing member is moved toward the first position after piercing the pledget, which is anchored at the pledget anchoring portion, by the needle. The pledget can be removed from the slit before the pledget arrives at the distal end of the side aperture, and thus the pledget can be easily removed.

In the above ligature and suture device for medical application, the pledget anchoring portion may be formed as a slit that is placed in the insertion portion, and taking a point that is punctured by the needles when the pledget is anchored in the slit as a needle puncture point, then if the shortest distance from an edge portion of the pledget to the needle puncture point is taken as D, and if the shortest distance from the slit to the needle puncture point is taken as "d", then the predetermined distance L is determined using a Formula:

$$L \geq (D^2 - d^2)^{1/2}.$$

In the ligature and suture device of the invention for medical application, because the pledget does not reach the distal end of the side aperture even when the distance from the slit to the needle puncture point is the minimum value "d" after the pledget is pierced by the needle and is moved toward the side aperture and immediately before being removed from the slit, the pledget can be removed from the slit before it reaches the side aperture.

The above ligature and suture device for medical application may further include jaw portions that are placed on a side surface of the slit, and that protrude gradually towards a terminal end side of the slit.

In the ligature and suture device of the invention for medical application, when the pledget is to be removed from the end of the aperture toward the outside of the distal end, the pledget will not easily come out because the pledget engages the jaw portions. On the other hand, when the pledget is to be removed from the end of the aperture toward the inside of the distal end, the pledget will easily come out while moving along the jaw portions.

The above ligature and suture device for medical application may further include a variable member that alters at least a portion of the width of the slit.

In the ligature and suture device of the invention for medical application, the width of the slit can be changed in accordance with the thickness of the pledget so that the pledget can be pressed in, and the width of the slit can be increased by adjusting the position of the variable member when the pledget is to be removed.

In the above ligature and suture device for medical application, the variable member may be provided with an elastic member that is placed on the side surface on the side aperture side of the slit and that is able to make contact with the pledget.

In the ligature and suture device of the invention for medical application, when the suturing member is moved toward the first position after piercing the pledget by the needle, the width of the slit can be increased by compressively deforming the variable member using the pledget, and thus the pledget can be easily removed.

The above ligature and suture device for medical application may further include: a pledget supporting portion that supports the pledget, and that is provided integrally with the distal end portion, and that is able to change the pledget from being aligned parallel to the needle to being aligned in a direction in which it can be pierced by the needle; and a deforming device that supplies deforming force to the pledget supporting portion.

In the ligature and suture device of the invention for medical application, it is possible to suppress interference between the endoscope and the pledget when the endoscope is inserted into the distal end portion, and only when the needle is inserted in the pledget is the deforming device operated and the pledget support portion deformed, so that the orientation of the pledget can be changed and the needle can be inserted in the pledget.

In the above ligature and suture device for medical application, the pledget supporting portion may be provided integrally with the distal end portion, and the deforming device is the suction device that is able to place the interior of the distal end portion under negative pressure.

In the ligature and suture device of the invention for medical application, only when the biomedical tissue is suctioned by the suction device is the pledget supporting portion deformed, so that the orientation of the pledget can be changed.

In the above ligature and suture device for medical application, the pledget supporting portion may be provided integrally with the distal end portion, and the deforming device may be a wire member having flexibility.

In the ligature and suture device of the invention for medical application, by operating the wire member at the moment of penetration by the needle, the pledget supporting portion can be deformed.

The ligature and suture system of the invention for medical application enables biomedical tissue that is being ligatured or sutured to be verified using an endoscope that has been inserted inside a lumen. In addition, after biomedical tissue has been suctioned by a suctioning device provided in the endoscope, the biomedical tissue can be ligatured or sutured via a pledget using a suturing member, and any burying of the suturing member in the biomedical tissue can be restrained.

In the ligature and suture method of the invention for medical application, after the biomedical tissue has been suctioned into the distal end portion by the suction device, the needle is inserted through both the biomedical tissue and the pledget, and these are sutured or ligatured by a suturing member. Therefore, it is possible to suppress any burying of the suturing member in the biomedical tissue.

According to the present invention, using this ligature and suture device for medical application, it is possible to cause biomedical tissue to bulge to a desired height, and a ligaturing or suturing condition can be maintained for a longer time than is the case conventionally.

(Additional Item)

A ligature and suture device for medical application that ligatures or sutures biomedical tissue that has been suctioned by a suction device using a suturing member, including: an insertion portion having a lumen into which an endoscope can be inserted, and a distal end portion that is connected to the lumen and in which at least one side aperture is provided; at least one hollow needle that is able to support inside itself the suturing member, and that is placed inside the insertion portion such that a tip of the hollow needle is able to move between a first position, which is on a base end side of the side aperture, and a second position, which is on a distal end side of the side aperture; an operating section that performs an operation to move the needle; and at least one pledget that can be penetrated by the needle, and that is placed in a vicinity of the distal end of the side aperture so as to be freely removable from the distal end portion, wherein a slit into which the pledget is able to be press-inserted is placed so as to be open to a side surface of the distal end portion between the side aperture and the second position, and the slit is positioned so as to intersect the lumen at an oblique direction and also such that a terminal end side extends on a slant to the side aperture side.

This ligature and suture device for medical applications enables the direction in which the slit extends to approach the movement direction of a suturing member, and when the suturing member is moved to the first position side after the pledget has been punctured by a needle, enables resistance to the slit when the pledget is being withdrawn to be reduced, and enables the pledget to be moved more easily along the slit.

What is claimed is:

1. A ligature and suture device for medical application that ligatures or sutures biomedical tissue that has been suctioned by a suction device using a suturing member, the ligature and suture device comprising:
   an insertion portion having a lumen into which an endoscope can be inserted, and a distal end portion that is connected to the lumen and in which at least one side aperture is provided;
   at least one hollow needle that is able to support inside itself the suturing member, and that is placed inside the insertion portion such that a tip of the hollow needle is able to move between a first position, which is on a base end side of the side aperture, and a second position, which is on a distal end side of the side aperture;
   an operating section that performs an operation to move the needle; and
   at least one pledget that can be penetrated by the needle, and that is placed in the distal end portion and closer to a tip of the distal end portion than the side aperture, so as to be freely removable from the distal end portion,
   the pledget has a semicircular shape, having a circular arc portion, and
   wherein the suturing member includes a string member and a holding member being provided at a distal end of the string member and holds the pledget against the biomedical tissue,
   wherein a slit into which the pledget can be press-inserted is provided so as to open onto a side surface of the distal end portion between the side aperture and the second position, and
   wherein, the pledget and the slit of the distal end portion are configured so that, when the pledget is press-inserted into the slit, the circular arc portion of the pledget is held by the distal end portion at the slit.

2. The ligature and suture device for medical application according to claim 1, wherein the pledget is placed between the distal end of the side aperture and the second position on a movement path of the needle.

3. The ligature and suture device for medical application according to claim 1, further comprising a protective member that protects a placement state of the pledget when the endoscope that has been inserted into the lumen is being operated.

4. The ligature and suture device for medical application according to claim 3, wherein the protective member is placed in the distal end portion.

5. The ligature and suture device for medical application according to claim 4, wherein the protective member is a restricting member that restricts contact between the endoscope that has been inserted into the lumen and the pledget.

6. The ligature and suture device for medical application according to claim 3, wherein the protective member is placed on the pledget.

7. The ligature and suture device for medical application according to claim 1, further comprising a distal end side needle guide portion that is placed further to the base end side of the distal end portion compared to the pledget, and that guides a distal end of the needle to the pledget.

8. The ligature and suture device for medical application according to claim 1, wherein a reinforcing portion that increases a rigidity of the distal end portion is provided in the distal end portion between at least the first position and the second position.

9. The ligature and suture device for medical application according to claim 1, wherein a reinforcing portion that increases a rigidity of the distal end portion is provided in the distal end portion between at least the first position and the distal end side needle guide portion.

10. The ligature and suture device for medical application according to claim 1, wherein
the insertion portion is provided with a pledget anchoring portion that anchors the pledget such that the pledget can be freely removed and anchored again, and
the pledget anchoring portion is formed such that, when the pledget is being moved, at least a portion of the pledget can be removed before the pledget arrives at a distal end of the side aperture, and the pledget anchoring portion is placed a predetermined distance apart from a distal end of the side aperture.

11. The ligature and suture device for medical application according to claim 10, wherein
the pledget anchoring portion is formed as a slit that is placed in the insertion portion, and
taking a point that is punctured by the needles when the pledget is anchored in the slit as a needle puncture point, then if the shortest distance from an edge portion of the pledget to the needle puncture point is taken as D, and if the shortest distance from the slit to the needle puncture point is taken as "d", then the predetermined distance L is determined using a Formula: $L \geqq (D^2 - d^2)^{1/2}$.

12. The ligature and suture device for medical application according to claim 1, further comprises jaw portions that are placed on a side surface of the slit, and that protrude gradually towards a terminal end side of the slit.

13. The ligature and suture device for medical application according to claim 1, further comprises a variable member that alters at least a portion of the width of the slit.

14. The ligature and suture device for medical application according to claim 13, wherein the variable member is provided with an elastic member that is placed on the side surface on the side aperture side of the slit and that is able to make contact with the pledget.

15. The ligature and suture device for medical application according to claim 1, further comprising:
a pledget supporting portion that supports the pledget, and that is provided integrally with the distal end portion, and that is able to change the pledget from being aligned parallel to the needle to being aligned in a direction in which it can be pierced by the needle; and
a deforming device that supplies deforming force to the pledget supporting portion.

16. The ligature and suture device for medical application according to claim 15, wherein the pledget supporting portion is provided integrally with the distal end portion, and the deforming device is the suction device that is able to place the interior of the distal end portion under negative pressure.

17. The ligature and suture device for medical application according to claim 15, wherein the pledget supporting portion is provided integrally with the distal end portion, and the deforming device is a wire member having flexibility.

18. A ligature and suture system for medical application, comprising:
the ligature and suture device for medical application according to claim 1; and
an endoscope having the suction device that can be inserted into the lumen.

19. A ligature and suture method for medical application that ligatures or sutures biomedical tissue that has been suctioned by a suction device using a suturing member,
the suturing member includes a string member and a holding member, the holding member being provided at a distal end of the string member and holds a semicircular shaped pledget against the biomedical tissue, and
the ligature and suture method uses an insertion portion having a lumen into which the endoscope can be inserted, and a distal end portion that is connected to the lumen and in which at least one side aperture is provided,
the ligature and suture method comprising:
a pledget holding process in which the pledget is press-inserted into a slit provided at the distal end portion, holding a circular arc portion of the pledget by the slit;
a suction process in which an endoscope is inserted into the insertion portion, and the biomedical tissue is suctioned from the side aperture into the distal end portion;
an insertion process in which at least one hollow needle that is able to support inside itself the suturing member, and that is placed inside the insertion portion such that a tip of the hollow needle is able to at least move between a first position, which is on a base end side of the side aperture, and a second position, which is on a distal end side of the side aperture is inserted into the biomedical tissue and into the pledget that is placed in the distal end portion and between the distal end of the side aperture and the second position on a movement path of the needle so as to be freely removable from the distal end portion;
a process in which the holding member of the suturing member is pushed out from inside the needle to the distal side of the pledget; and
a process in which suturing or ligaturing is performed using the suturing member by withdrawing the needle from the biomedical tissue.

20. The ligature and suture device for medical application according to claim 1, wherein the pledget is provided in the distal end portion at least when the biomedical tissue is suctioned.

* * * * *